US011864925B2

(12) United States Patent
Muse et al.

(10) Patent No.: US 11,864,925 B2
(45) Date of Patent: Jan. 9, 2024

(54) MACHINE LEARNING TECHNIQUES FOR DETECTING SPLINTING ACTIVITY

(71) Applicant: UnitedHealth Group Incorporated, Minnetonka, MN (US)

(72) Inventors: Jon Kevin Muse, Thompsons Station, TN (US); Marilyn L. Gordon, Cherry Hill, NJ (US); Komal Khatri, Cedar Park, TX (US); Gregory J. Boss, Saginaw, MI (US)

(73) Assignee: UnitedHealth Group Incorporated, Minnetonka, MN (US)

( * ) Notice: Subject to any disclaimer, the term of this patent is extended or adjusted under 35 U.S.C. 154(b) by 198 days.

(21) Appl. No.: 17/375,627

(22) Filed: Jul. 14, 2021

(65) Prior Publication Data

US 2023/0020331 A1    Jan. 19, 2023

(51) Int. Cl.
*A61B 5/00*       (2006.01)
*G06N 20/00*      (2019.01)
*G16H 40/67*      (2018.01)
*G16H 50/70*      (2018.01)
*A61B 5/113*      (2006.01)
*G16H 50/30*      (2018.01)
*A61B 5/08*       (2006.01)
*G16H 50/20*      (2018.01)

(52) U.S. Cl.
CPC ......... *A61B 5/7267* (2013.01); *A61B 5/0816* (2013.01); *A61B 5/1135* (2013.01); *A61B 5/4824* (2013.01); *A61B 5/7275* (2013.01); *G06N 20/00* (2019.01); *G16H 40/67* (2018.01); *G16H 50/20* (2018.01); *G16H 50/30* (2018.01); *G16H 50/70* (2018.01)

(58) Field of Classification Search
CPC ... A61B 5/7267; A61B 5/0816; A61B 5/1135; A61B 5/4824; A61B 5/7275; G06N 20/00; G16H 40/67; G16H 50/20; G16H 50/30; G16H 50/70
See application file for complete search history.

(56) References Cited

U.S. PATENT DOCUMENTS

| 9,017,256 B2 | 4/2015 | Gottesman |
| 9,282,893 B2 | 3/2016 | Longinotti-Buitoni et al. |
| 9,411,936 B2 | 8/2016 | Landrum et al. |
| 9,962,088 B2 | 5/2018 | Palani |

(Continued)

OTHER PUBLICATIONS

"Atelectasis—Symptoms and Causes," Mayo Clinic, (4 pages), (online), [Retrieved from the Internet Sep. 29, 2021] <URL: https://www.mayoclinic.org/diseases-conditions/atelectasis/symptoms-causes/syc-20369684?p=1>.

(Continued)

*Primary Examiner* — Eric F Winakur
*Assistant Examiner* — Jonathan Drew Moroneso
(74) *Attorney, Agent, or Firm* — Alston & Bird LLP

(57) ABSTRACT

Various embodiments of the present invention provide methods, apparatus, systems, computing devices, computing entities, and/or the like for performing splinting activity detection. Certain embodiments of the present invention utilize systems, methods, and computer program products that perform splinting activity detection using at least one of splinting activity detection machine learning models, observed inspiration-expiration waveform pattern, and expected inspiration-expiration waveform patterns.

20 Claims, 11 Drawing Sheets

(56) References Cited

U.S. PATENT DOCUMENTS

| | | | |
|---|---|---|---|
| 10,271,739 | B2 | 4/2019 | Freeman et al. |
| 10,349,893 | B2 | 7/2019 | Lee et al. |
| 10,531,832 | B2 | 1/2020 | Reuveny |
| 10,898,718 | B2 | 1/2021 | Srivastava et al. |
| 2015/0087926 | A1 | 3/2015 | Raz et al. |
| 2018/0015282 | A1* | 1/2018 | Waner ............... A61B 5/00 |
| 2019/0015614 | A1* | 1/2019 | Alahmadi ........... A61B 5/082 |
| 2020/0135334 | A1* | 4/2020 | Rajasekhar .......... G10L 15/26 |
| 2022/0020488 | A1* | 1/2022 | Kennedy ............ G16H 20/40 |
| 2022/0104724 | A1* | 4/2022 | Cates ............. A61B 5/02233 |
| 2023/0000428 | A1* | 1/2023 | Pinczuk ............ A61F 5/3707 |

OTHER PUBLICATIONS

"Atelectasis," Wikipedia, (6 pages), (online), [Retrieved from the Internet Sep. 29, 2021] <https://en.wikipedia.org/wiki/Atelectasis>.
Dadonaite, Bernadeta et al. "Pneumonia," Our World In Data, published online Nov. 2019, (21 pages), [Retrieved from the Internet Sep. 29, 2021] <URL: https://ourworldindata.org/pneumonia>.
Hilbert, Janet et al. "Patient-Centered Care In Obstructive Sleep Apnea: A Vision For The Future," Sleep Medicine Reviews, Feb. 2018, vol. 37, pp. 138-147, DOI: 10.1016/j.smrv.2017.02.004, (Published online: Feb. 24, 2017, DOI: 10.1016/j.smrv.2017.02.004), PMID: 28633915, PMCID: PMC6006997.

* cited by examiner

Identify observed breathing pattern sensory data for a monitored individual
601

Determine an observed inspiration-expiration waveform pattern based on the observed breathing pattern sensory data
602

Generate, by utilizing a splinting activity detection machine learning model, a predicted interruption score for the observed breathing pattern sensory data based at least in part on the observed inspiration-expiration waveform pattern and one or more expected inspiration-expiration waveform patterns
603

Perform one or more prediction-based actions based on the predicted interruption score
604

FIG. 6

MACHINE LEARNING TECHNIQUES FOR DETECTING SPLINTING ACTIVITY

BACKGROUND

Various embodiments of the present invention address technical challenges related to performing health-related detection. Various embodiments of the present invention disclose innovative techniques for efficiently and effectively performing health-related detection using various predictive data analysis techniques.

BRIEF SUMMARY

In general, various embodiments of the present invention provide methods, apparatus, systems, computing devices, computing entities, and/or the like for performing splinting activity detection. Certain embodiments of the present invention utilize systems, methods, and computer program products that perform splinting activity detection using at least one of splinting activity detection machine learning models, observed inspiration-expiration waveform pattern, and expected inspiration-expiration waveform patterns.

In accordance with one aspect, a method is provided. In one embodiment, the method comprises: identifying observed breathing pattern sensory data for a monitored individual; determining an observed inspiration-expiration waveform pattern based at least in part on the observed breathing pattern sensory data; generating, by utilizing a splinting activity detection machine learning model, a predicted interruption score for the observed breathing pattern sensory data, wherein: (i) the splinting activity detection machine learning model is characterized by one or more expected inspiration-expiration waveform patterns, and (ii) the predicted interruption score is generated at least in part by comparing the observed inspiration-expiration waveform pattern with the one or more expected inspiration-expiration waveform patterns; and performing one or more prediction-based actions based at least in part on the predicted interruption score.

In accordance with another aspect, a computer program product is provided. The computer program product may comprise at least one computer-readable storage medium having computer-readable program code portions stored therein, the computer-readable program code portions comprising executable portions configured to: identify observed breathing pattern sensory data for a monitored individual; determine an observed inspiration-expiration waveform pattern based at least in part on the observed breathing pattern sensory data; generate, by utilizing a splinting activity detection machine learning model, a predicted interruption score for the observed breathing pattern sensory data, wherein: (i) the splinting activity detection machine learning model is characterized by one or more expected inspiration-expiration waveform patterns, and (ii) the predicted interruption score is generated at least in part by comparing the observed inspiration-expiration waveform pattern with the one or more expected inspiration-expiration waveform patterns; and perform one or more prediction-based actions based at least in part on the predicted interruption score.

In accordance with yet another aspect, an apparatus comprising at least one processor and at least one memory including computer program code is provided. In one embodiment, the at least one memory and the computer program code may be configured to, with the processor, cause the apparatus to: identify observed breathing pattern sensory data for a monitored individual; determine an observed inspiration-expiration waveform pattern based at least in part on the observed breathing pattern sensory data; generate, by utilizing a splinting activity detection machine learning model, a predicted interruption score for the observed breathing pattern sensory data, wherein: (i) the splinting activity detection machine learning model is characterized by one or more expected inspiration-expiration waveform patterns, and (ii) the predicted interruption score is generated at least in part by comparing the observed inspiration-expiration waveform pattern with the one or more expected inspiration-expiration waveform patterns; and perform one or more prediction-based actions based at least in part on the predicted interruption score.

BRIEF DESCRIPTION OF THE DRAWINGS

Figure 1:
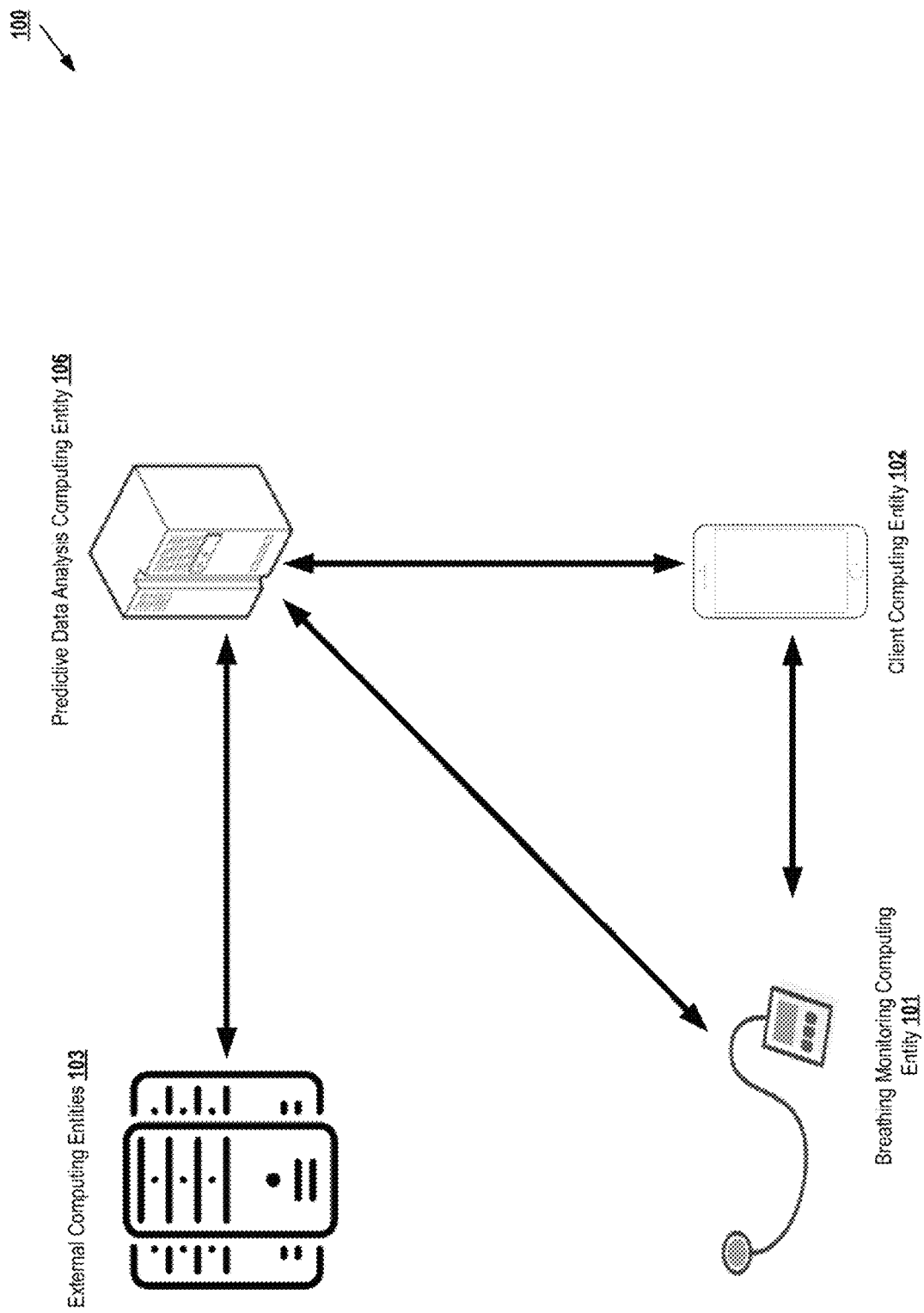

Having thus described the invention in general terms, reference will now be made to the accompanying drawings, which are not necessarily drawn to scale, and wherein:

FIG. 1 provides an exemplary overview of a hardware architecture that can be used to practice embodiments of the present invention.

Figure 2:
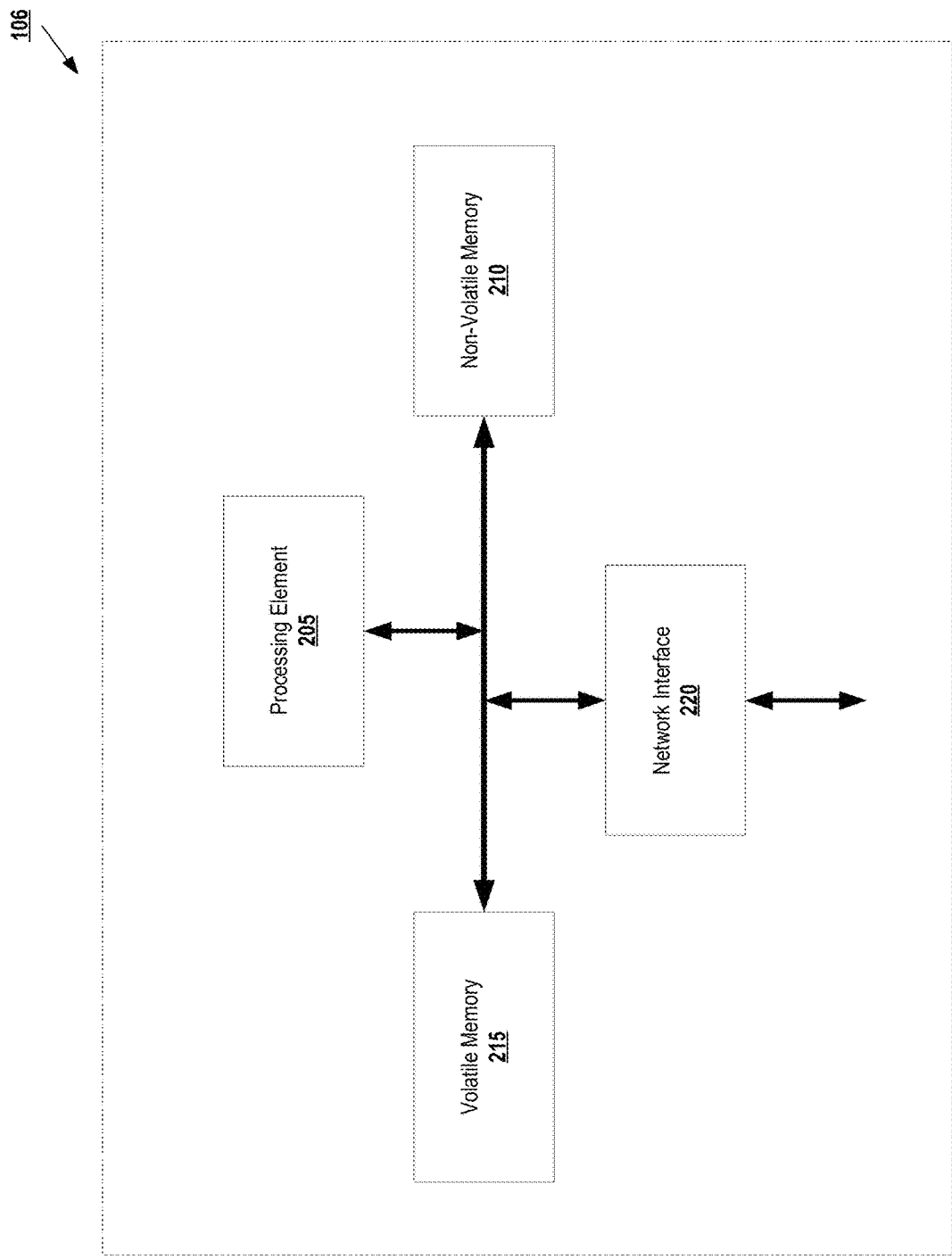

FIG. 2 provides an example predictive data analysis computing entity, in accordance with some embodiments discussed herein.

Figure 3:
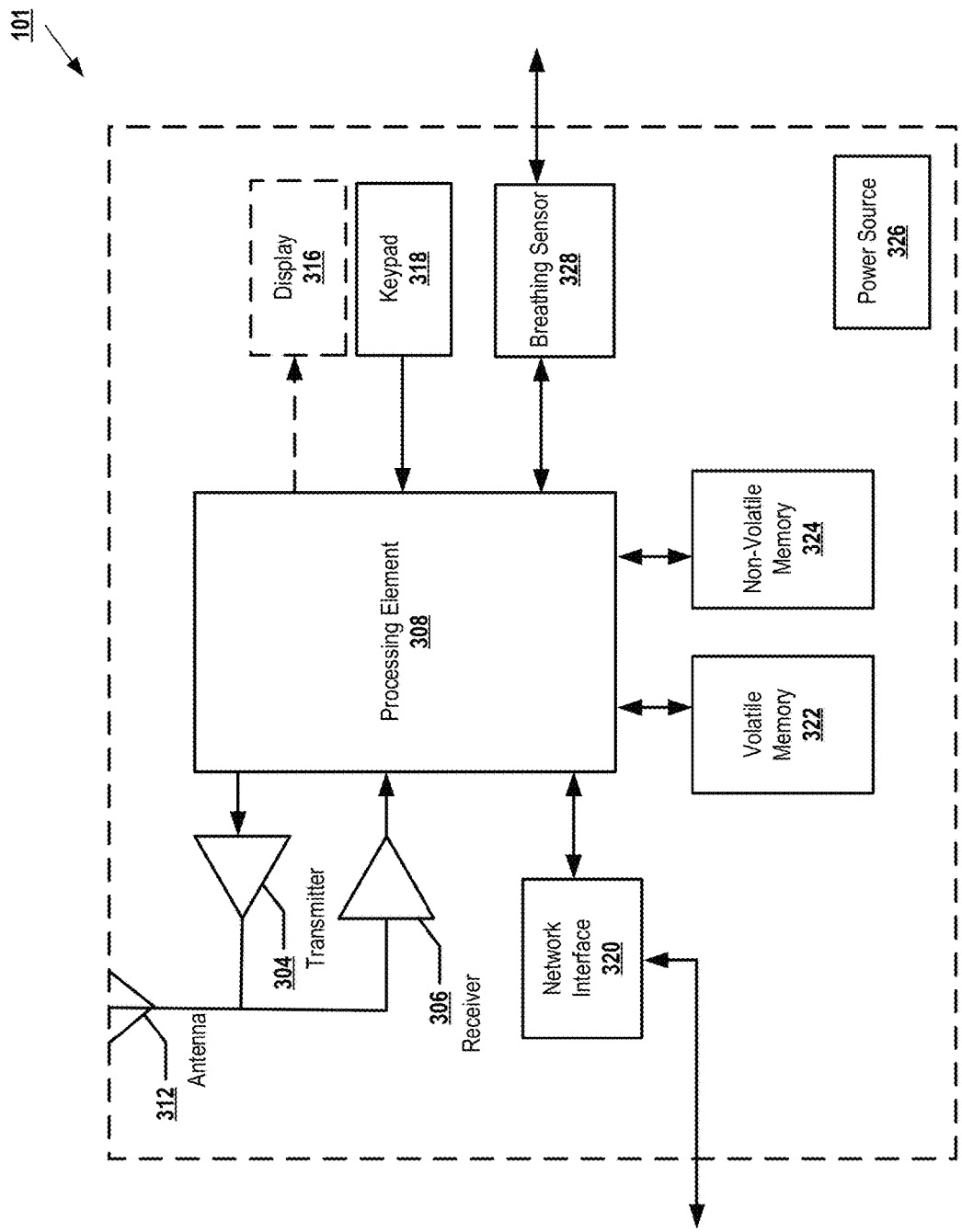

FIG. 3 provides an example breathing monitoring computing entity, in accordance with some embodiments discussed herein.

Figure 4:
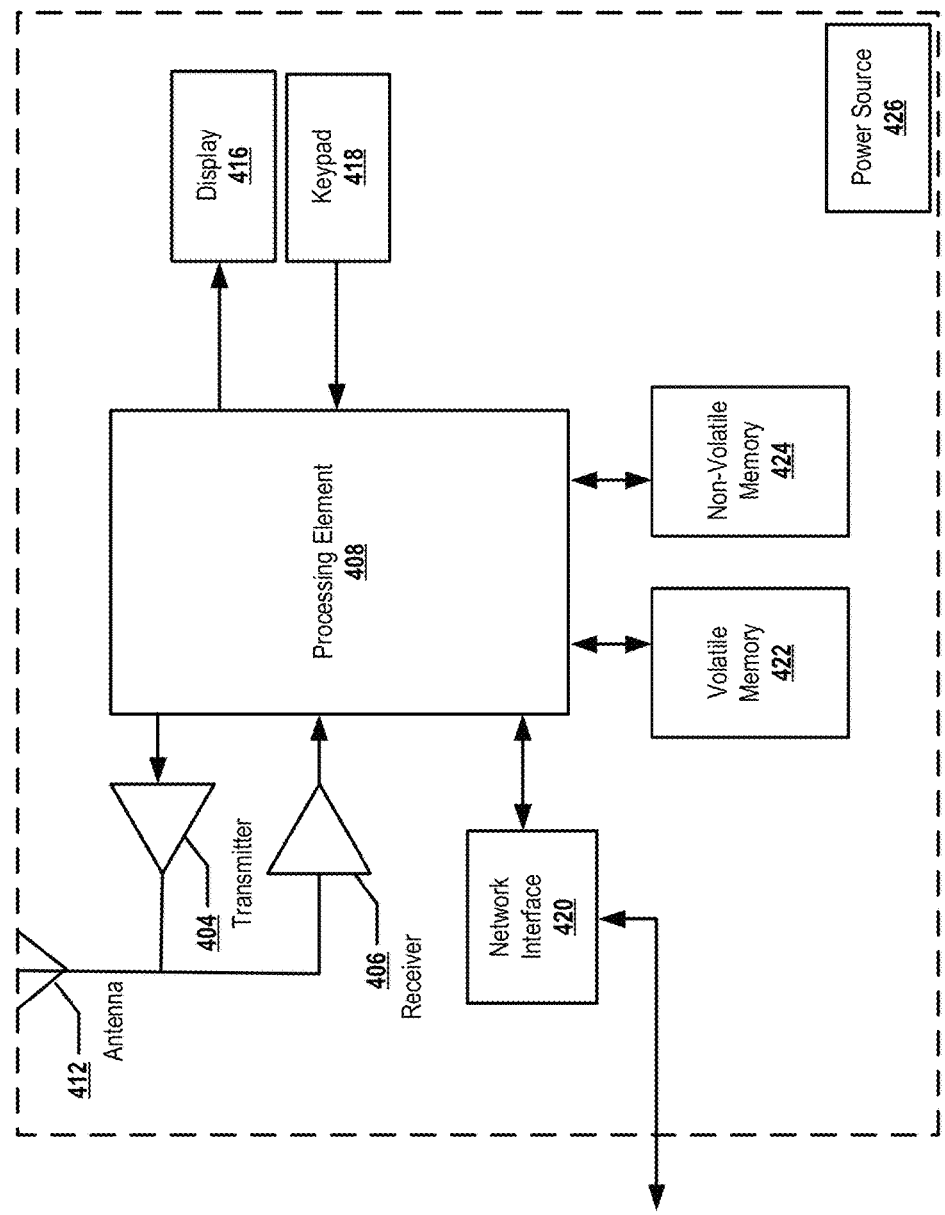

FIG. 4 provides an example client computing entity, in accordance with some embodiments discussed herein.

Figure 5:
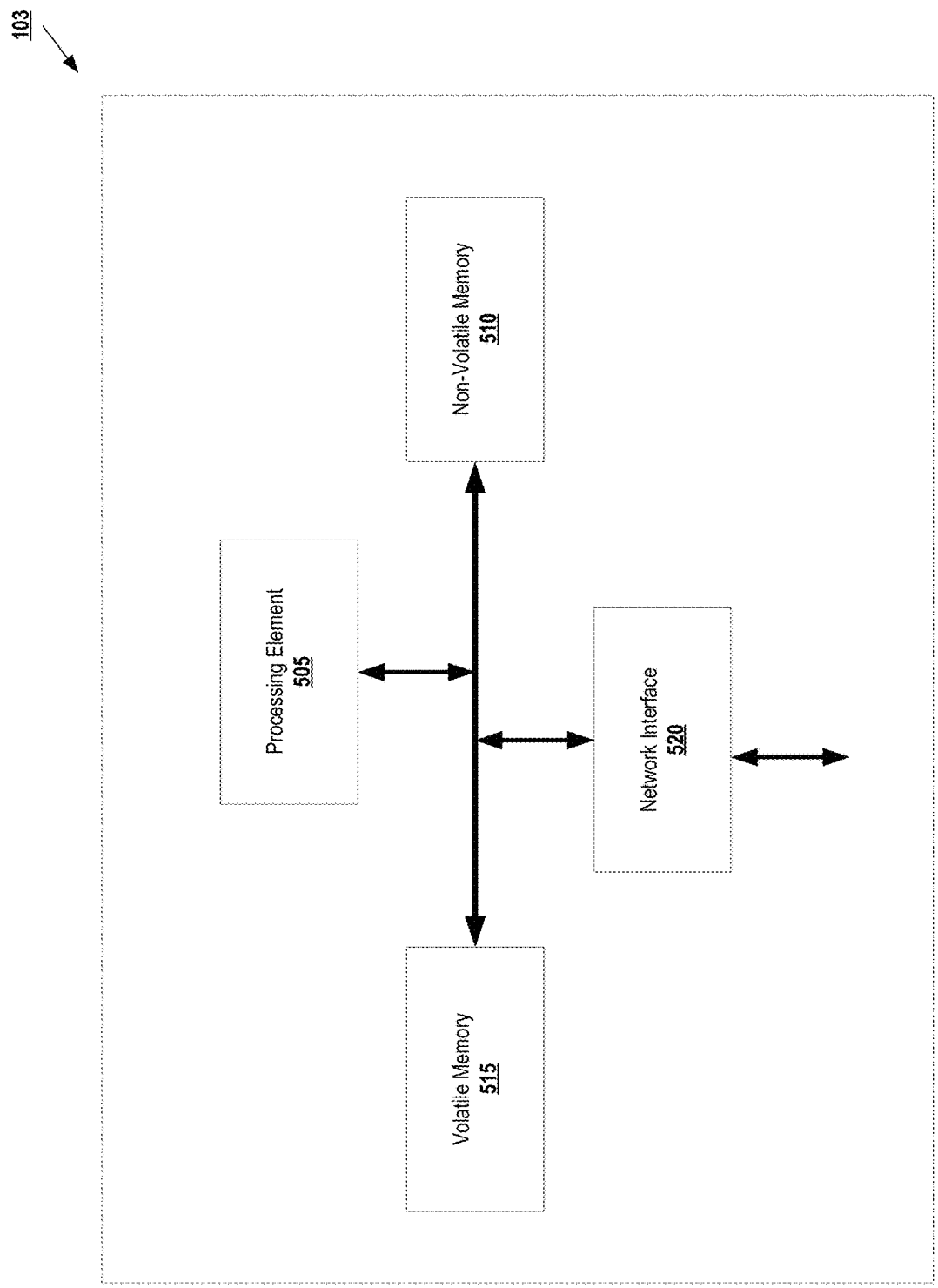

FIG. 5 provides an example external computing entity, in accordance with some embodiments discussed herein.

FIG. 6 is a flowchart diagram of an example process for machine-learning-based splinting activity detection activity, in accordance with some embodiments discussed herein.

Figure 7:
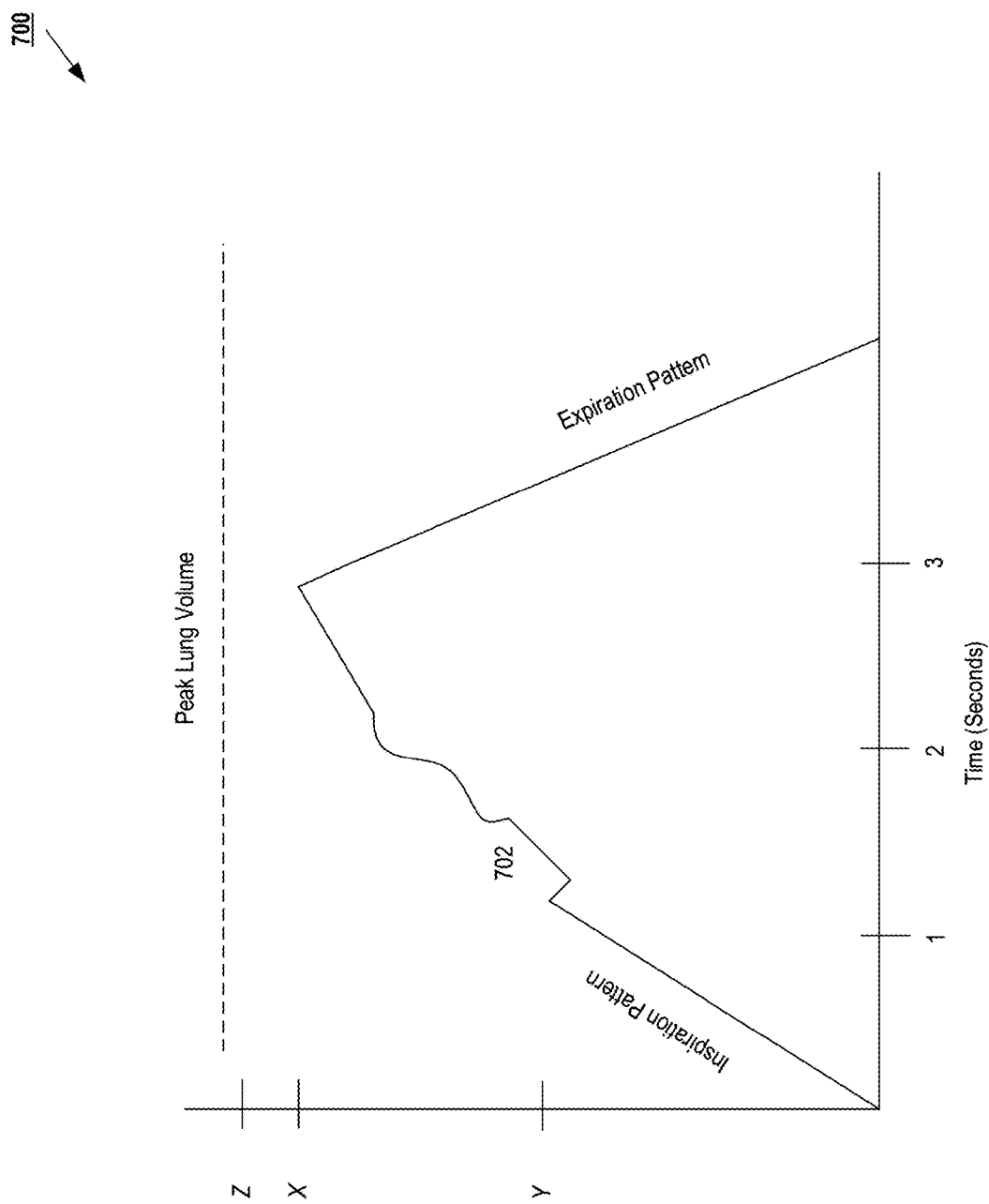

FIG. 7 provides an operational example of an observed inspiration-expiration waveform pattern, in accordance with some embodiments discussed herein.

Figure 8:
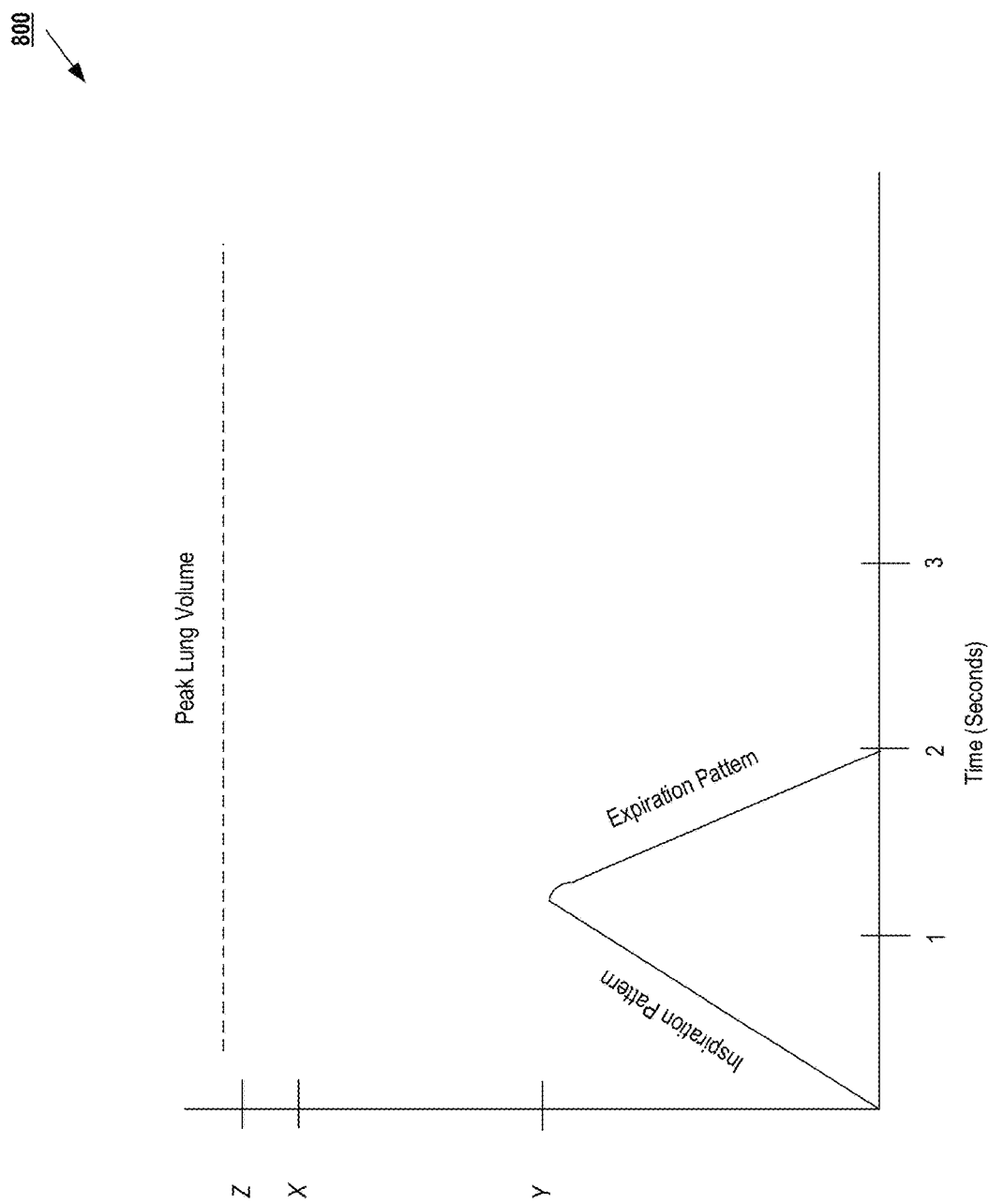

FIG. 8 provides an operational example of an observed inspiration-expiration waveform pattern, in accordance with some embodiments discussed herein.

Figure 9:
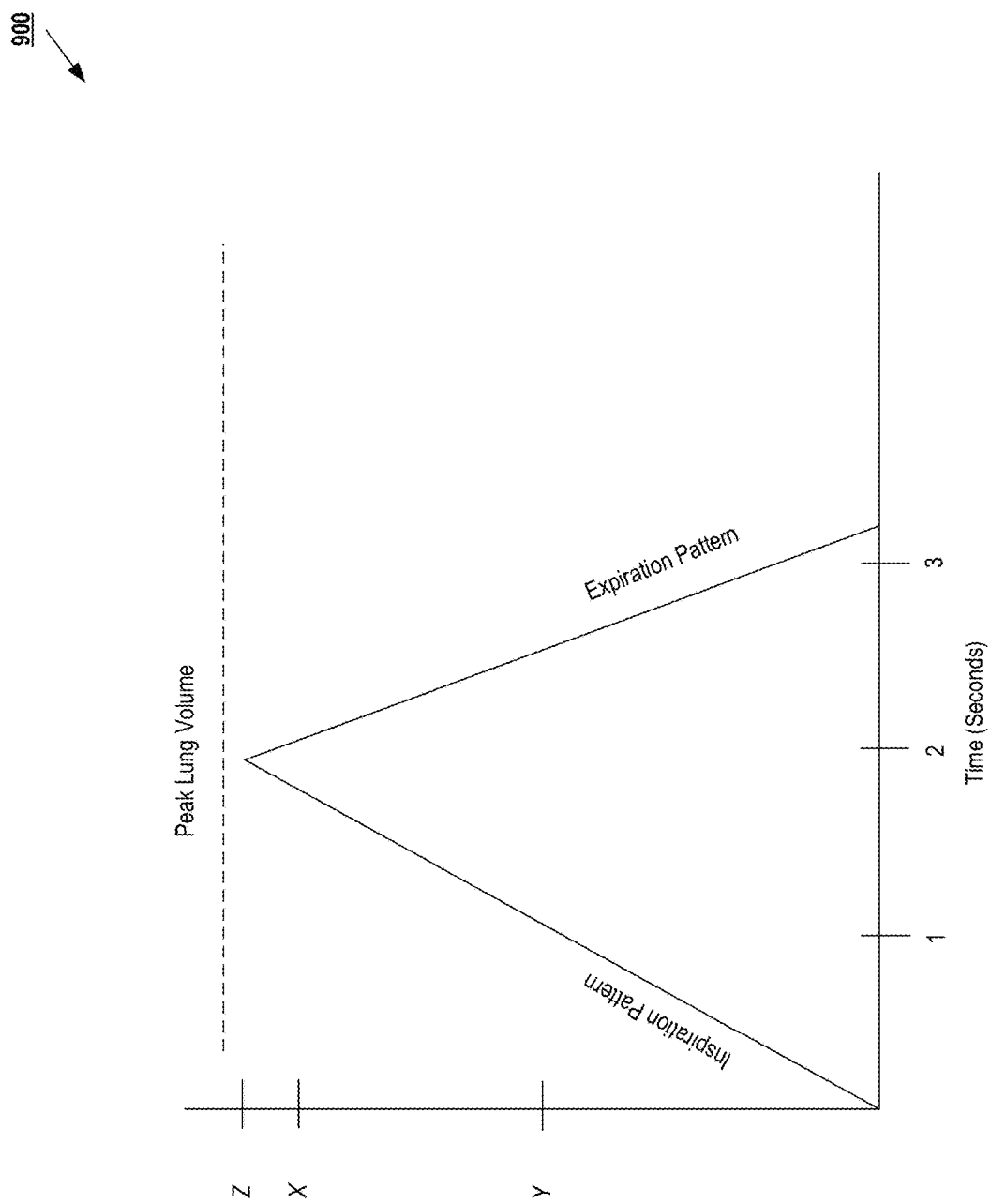

FIG. 9 provides an operational example of an expected inspiration-expiration waveform pattern, in accordance with some embodiments discussed herein.

Figure 10:
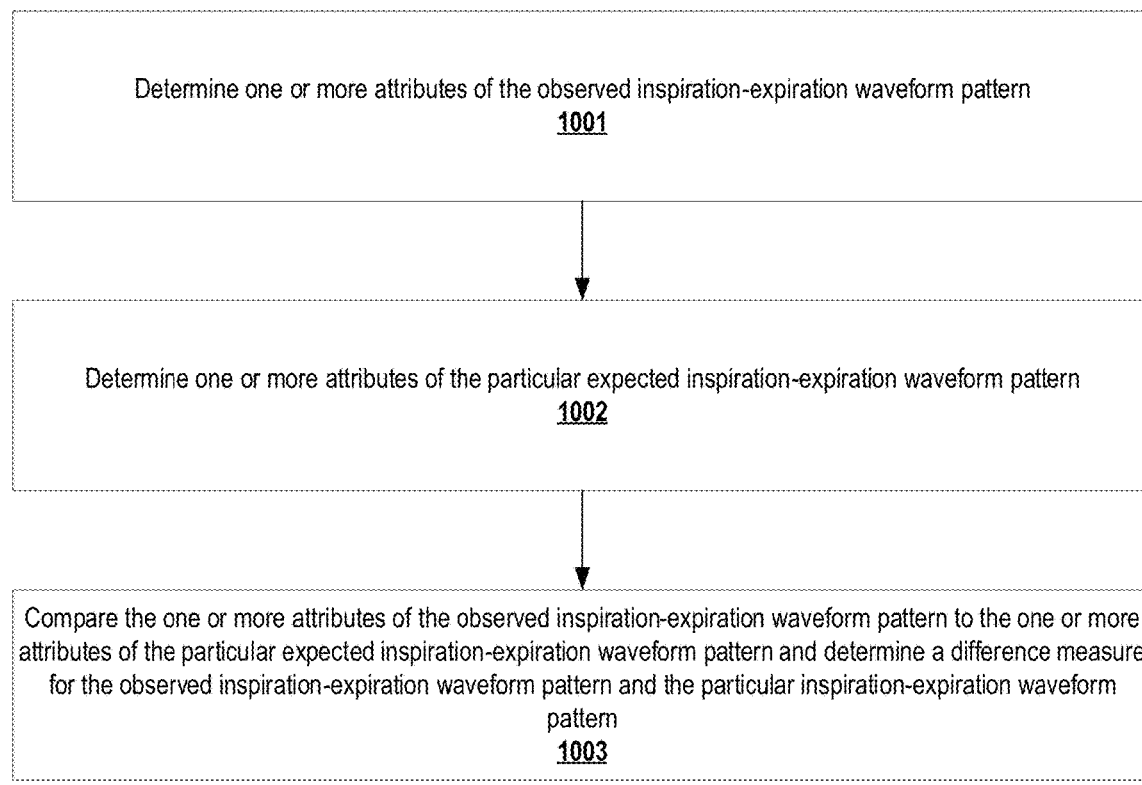

FIG. 10 is a flow chart diagram of an example process for determining an interruption score based at least in part on comparing an observed inspiration-expiration waveform pattern to a particular inspiration expiration waveform pattern, in accordance with some embodiments discussed herein.

Figure 11:
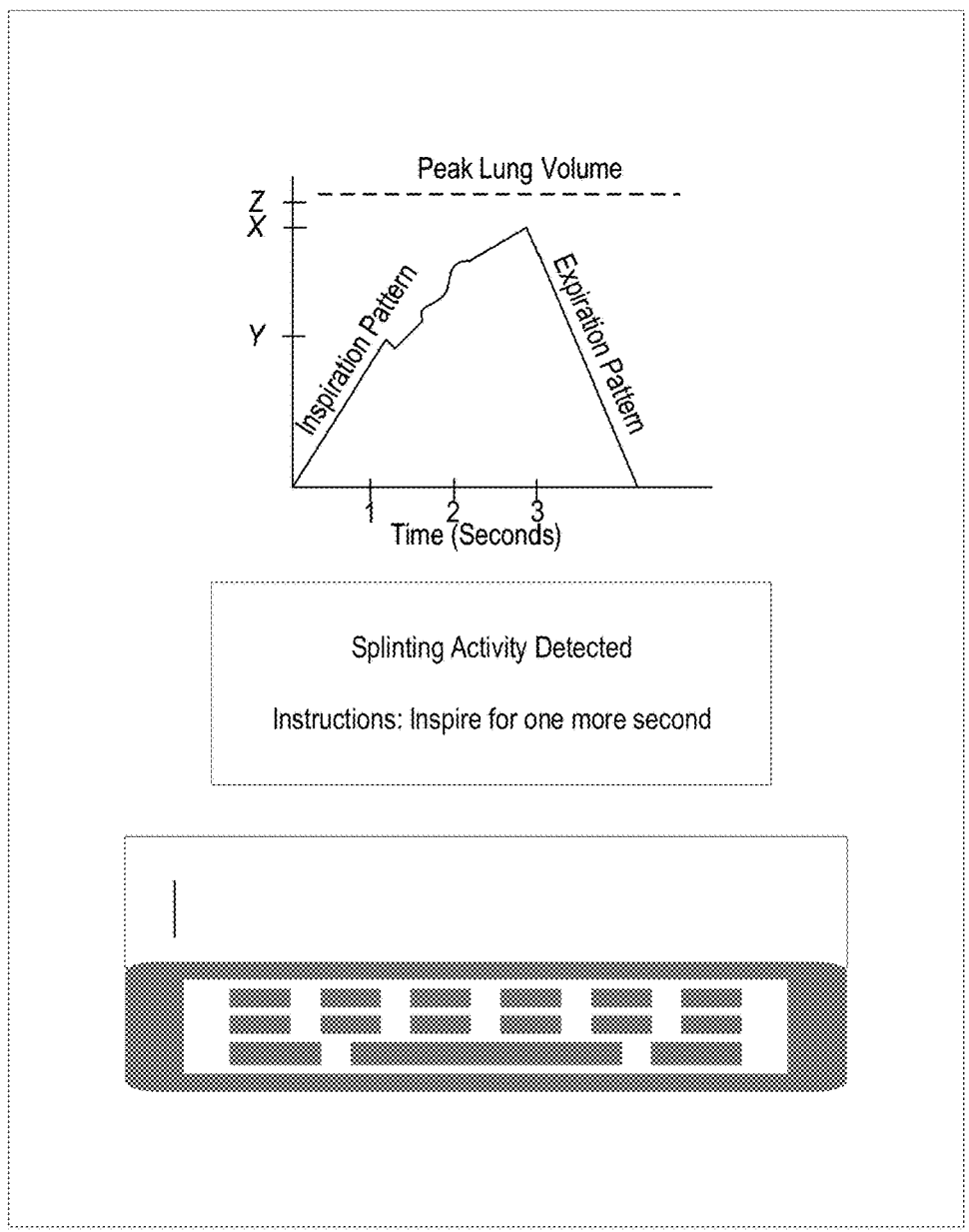

FIG. 11 provides an example user interface for receiving one or more therapeutic notifications, in accordance with some embodiments discussed herein.

DETAILED DESCRIPTION

Various embodiments of the present invention now will be described more fully hereinafter with reference to the accompanying drawings, in which some, but not all, embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout. Moreover, while certain embodiments of the present invention are described with reference to predictive data analysis, one of ordinary skill in the art will recognize that the disclosed concepts can be used to perform other types of data analysis.

I. OVERVIEW AND TECHNICAL IMPROVEMENTS

Various embodiments of the present invention address technical challenges related to efficiently and effectively performing splinting activity detection based at least in part on observed breathing pattern sensory data for a monitored individual. The disclosed techniques improve the efficiency and effectiveness of splinting activity detection by utilizing a splinting activity detection machine learning model that is configured to compare an observed inspiration-expiration waveform pattern that is generated based at least in part on observed breathing pattern sensory data with the one or more expected inspiration-expiration waveform patterns. The splinting activity detection machine learning models utilize comparison operations that may, in at least some embodiments, reduce or eliminate the need for computationally expensive training operations in order to generate the noted splinting activity detection machine learning models. By reducing or eliminating the noted training operations, various embodiments of the present invention: (i) reduces or eliminates the computational operations needed for training and thus improves the computational efficiency of performing splinting activity detection, (ii) reduces or eliminates the need for storage resources to train/generate splinting activity detection machine learning models and thus improves storage efficiency of performing splinting activity detection, and (iii) reduces or eliminates the need for transmitting extensive training data needed to generate splinting activity detection machine learning models and thus improves transmission/network efficiency of performing splinting activity detection. Via the noted advantages, various embodiments of the present invention make substantial technical contributions to the fields of splinting activity detection in particular and healthcare-related predictive data analysis in general.

An exemplary application of various embodiments of the present invention relates to proactively monitoring breathing patterns of atelectasis patients. Atelectasis is one of the most common breathing (respiratory) complications after surgery. Patients generally will experience some form of pain when breathing. Atelectasis causes splinting in the body's effort to avoid pain. Improper breathing exercises or the lack of (with or without an incentive spirometer) can cause complications most commonly resulting in pneumonia, which can lead to death. Besides post-surgical patients, acute lung conditions or even those that are chronic put the patient at risk for lung pain that can result in serious illness or death if the patient does not follow proper lung care guidance. Concerning lung pain due to atelectasis or pleurisy, the patient may not be aware that they are coddling or compensating physically or mentally right away. Older patients and much younger patients at each end of the age spectrum are particularly at risk of this condition.

II. DEFINITIONS

The term "observed breathing pattern sensory data" may refer to a data object that describes one or more instances of breathing measurements for a corresponding monitored individual, where each instance of breathing measurements is associated with a corresponding inspiration-expiration cycle of the monitored individual. Examples of breathing measurements may include voltage signals corresponding to the inspiration and expiration of a monitored individual. In an example embodiment, the observed breathing pattern sensory data may be calculated using one or more breathing sensors, where the breathing sensors are configured to record breathing measurements and to transmit (e.g., wirelessly, through a wired transmission medium, and/or the like) the recorded breathing measurements to a computing device configured to store the breathing measurements and/or determine an inspiration-expiration waveform pattern based at least in part on the breathing measurements. Examples of breathing sensors may include breathing sensors that are in direct contact with the monitored individual's body as well as breathing sensors that are not in direct contact with the monitored individual's body. For example, breathing sensors may be integrated and/or secured to a wearable device (e.g., a vest, shirt, body band, and/or the like). In example embodiments, the breathing sensors may include a stretch sensor integrated and/or secured to a stretchable wearable device positioned with respect to the diaphragm of the monitored individual, where the stretch sensor measures voltage signals corresponding to the stretch of the wearable device as the diaphragm of the monitored individual contracts and expands. In example embodiments, the observed breathing pattern sensory data may be associated with an activity severity level of one or more activity severity levels. The one or more activity severity levels may be associated with one or more user activity events. Examples of user activity events may include sleep events, exercise events, and/or the like. In some example embodiments, the one or more activity severity levels and/or user activity event may be determined based at least in part on biometric data (e.g., heart rate data, pulse data, and/or the like).

The term "observed inspiration-expiration waveform pattern" may refer to a data object that describes a graph representation of an inspiration-expiration cycle of a corresponding monitored individual that is generated by processing the breathing pattern sensory data for the corresponding monitored individual. For example, a portion of the observed inspiration-expiration waveform pattern may represent the observed inspiration of the corresponding monitored individual and another portion of the observed inspiration-expiration waveform pattern may represent the observed expiration of the corresponding monitored individual. For example, in some embodiments, an observed inspiration-expiration waveform pattern may be substantially triangular, where the left portion (e.g., the left half) of the substantially triangular observed inspiration-expiration waveform pattern describes the observed inspiration pattern for the observed breathing pattern sensory data of the monitored individual and the right portion (e.g., the right half) of the substantially triangular observed inspiration-expiration waveform pattern describes the observed expiration for the observed breathing pattern sensory data of the monitored individual. An observed inspiration-expiration waveform pattern may comprise one or more attributes (e.g., an observed peak inspiration, a time from the beginning of the observed inspiration-expiration waveform pattern to the observed peak inspiration of the observed inspiration-expiration waveform pattern, a time from the observed peak inspiration of the observed inspiration-expiration waveform pattern to the end of the observed inspiration-expiration waveform pattern, and/or the like), where the predicted interruption score for a monitored individual may be determined based at least in part on the one or more attributes. In an example embodiment, an observed inspiration-expiration waveform pattern may comprise a single observed inspiration-expiration cycle of the monitored individual. In some embodiments, an observed inspiration-expiration waveform pattern may comprise a plurality of inspiration-expiration cycles of the monitored individual over a period of time.

The term "expected inspiration-expiration waveform pattern" may refer to a data object that describes a graph representation of an expected inspiration-expiration cycle for a corresponding monitored individual. For example, an expected inspiration-expiration waveform pattern may be generated by processing breathing pattern sensory data collected during a known normal breathing period of the monitored individual. The breathing measurements of the monitored individual may be measured when the individual inspires and expires without an interruption in the inspiration-expiration cycle that is indicative of splinting activity. In an example embodiment, the breathing measurements may be measured under the supervision of a physician, a nurse, and/or the like. In some embodiments, the breathing measurements may be measured over a period of time. An example inspiration-expiration waveform pattern may be substantially triangular, where the left portion (e.g., the left half) of the substantially triangular expected inspiration-expiration waveform pattern describes the inspiration of the monitored individual and the right portion (e.g., the right half) of the substantially triangular expected inspiration-expiration waveform pattern describes the expiration of the monitored individual. An observed inspiration-expiration waveform pattern may comprise one or more attributes (e.g., expected peak inspiration, a time from the beginning of the expected inspiration-expiration waveform pattern to the expected peak inspiration of the observed inspiration-expiration waveform pattern, a time from the expected peak inspiration of the expected inspiration-expiration waveform pattern to the end of the expected inspiration-expiration waveform pattern, and/or the like). where a predicted interruption score for an observed breathing pattern sensory data of the monitored individual may be generated based at least in part on the one or more attributes.

The term "splinting activity detection machine learning model" may refer to a data object that is configured to describe parameters, hyper-parameters, and/or defined operations of a model that is configured to generate a predicted interruption score for a monitored individual in relation to a corresponding inspiration-expiration cycle based at least in part on an observed inspiration-expiration waveform pattern for the monitored individual. In some embodiments, the splinting activity detection machine learning model is a supervised machine learning model (e.g., a neural network model) that is trained using labeled data, where the supervised machine learning model is configured to generate a predicted interruption score, where the predicted interruption score is configured to be used to determine a recommended prediction-based action for a monitored individual. In some embodiments, the splinting activity detection machine learning model is an unsupervised machine learning model (e.g., a clustering model). In some embodiments, the inputs to a splinting activity detection machine learning model include an observed inspiration-expiration waveform pattern, which may be a vector or a matrix. In some embodiments, the outputs of a splinting activity detection machine learning model may include a predicted interruption score, which may be an atomic value or a vector.

The term "machine learning model" may refer to a data object that describes parameters, hyper-parameters, defined operations, and/or defined mappings of a model that is configured to process one or more prediction input values (e.g., one or more selected breathing measurements) in accordance with one or more trained parameters of the machine learning models in order to generate a prediction. An example of a machine learning model is a mathematically derived algorithm (MDA). An MDA may comprise any algorithm trained using training data to predict one or more outcome variables. Without limitation, an MDA, as used herein, may comprise machine learning frameworks including neural networks, support vector machines, gradient boosts, Markov models, adaptive Bayesian techniques, and statistical models (e.g., timeseries-based forecast models such as autoregressive models, autoregressive moving average models, and/or an autoregressive integrating moving average models). Additionally and without limitation, an MDA, as used in the singular, may include ensembles using multiple machine learning and/or statistical techniques.

The term "predicted interruption score" may refer to a data entity that is configured to describe a value that in turn describes the likelihood that a corresponding observed inspiration-expiration waveform pattern represents splinting activity. The predicted interruption score may be generated by a trained splinting activity detection machine learning model by processing an observed inspiration-expiration waveform pattern for a corresponding monitored individual. For example, the predicted interruption score for a particular monitored individual may be generated by comparing the observed inspiration waveform pattern with one or more expected inspiration-expiration waveform patterns, processing utilizing a trained splinting activity detection machine learning model. The predicted interruption score may be a Boolean value (e.g., where a one-valued predicted interruption score may represent that a corresponding observed inspiration-expiration waveform pattern includes splinting activity, while a zero-valued predicted interruption score may represent that the corresponding observed inspiration-expiration waveform pattern does not include splinting activity). In example embodiments, the predicted interruption score may be a non-Boolean value. In various embodiments, the predicted interruption score may be a vector. A predicted interruption score may be an output of a machine learning model. In some embodiments, the predicted interruption score for an observed inspiration-expiration waveform is determined by comparing the observed inspiration-expiration waveform pattern with the one or more expected inspiration-expiration waveform patterns. In some of the noted embodiments, comparing the observed inspiration-expiration waveform pattern with a particular expected inspiration-expiration waveform pattern of the one or more expected inspiration-expiration waveform patterns comprises determining, using the one or more processors, an observed peak amplitude of the observed inspiration-expiration waveform pattern; determining, using the one or more processors, an expected peak amplitude of the particular expected inspiration-expiration waveform pattern; and comparing the observed peak amplitude and the expected peak amplitude to determine a difference measure for the observed inspiration-expiration waveform pattern and the particular expected inspiration-expiration waveform pattern. In some embodiments, the predicted interruption score is determined based at least in part on whether a lowest difference measure associated with the observed inspiration-expiration waveform pattern satisfies a difference measure threshold. In some embodiments, a predicted interruption score describes whether an observed inspiration-expiration waveform pattern represents normal breathing, partial splinting, full splinting, etc.

The term "splinting activity" may refer to a data object that describes an occurrence of splinting (e.g., pain) in breathing of a monitored individual that may be determined by a trained splinting activity detection machine learning model by processing an observed inspiration-expiration waveform pattern for a corresponding monitored individual. In some embodiments, splinting activity for a particular monitored individual may be determined by processing (e.g., using a trained splinting activity detection machine learning model) the observed inspiration-expiration waveform pattern for the particular monitored individual as determined based at least in part on comparing one or more attributes of the observed inspiration-expiration waveform pattern for the particular monitored individual to one or more attributes of the expected inspiration-expiration waveform pattern of the particular monitored individual.

III. COMPUTER PROGRAM PRODUCTS, METHODS, AND COMPUTING ENTITIES

Embodiments of the present invention may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of an apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

IV. EXEMPLARY SYSTEM ARCHITECTURE

FIG. 1 depicts an architecture 100 for performing machine-learning-based splinting activity detection. The architecture includes a predictive data analysis computing entity 106, a breathing monitoring computing entity 101, a client computing entity 102, and/or one or more external computing entities 103. Communication between the noted computing entities may be facilitated using one or more communication networks. Examples of communication networks comprise any wired or wireless communication network including, for example, a wired or wireless local area network (LAN), personal area network (PAN), metropolitan area network (MAN), wide area network (WAN), short-range communication networks (e.g., Bluetooth networks), or the like, as well as any hardware, software and/or firmware required to implement it (such as, e.g., network routers, and/or the like).

The predictive data analysis computing entity 106 may be configured to receive observed breathing pattern sensory data from the breathing monitoring computing entity 101, process the observed breathing pattern sensory data to determine one or more prediction-based actions, and perform one or more prediction-based actions. In some embodiments, the predictive data analysis computing entity 106 may be configured to perform the one or more prediction-based actions by interacting with at least one of the breathing monitoring computing entity 101, the client computing entity 102, and the external computing entities 103.

For example, the predictive data analysis computing entity 106 may communicate splinting activity predictions generated based at least in part on the observed breathing pattern sensory data to the client computing entity 102 and/or the external computing entities 103. As another example, the predictive data analysis computing entity 106 may communicate one or more predicted interruption scores for one or more observed breathing pattern sensory data to the client computing entity 102 and/or the external computing entities 103. In some embodiments, some or all of the functions of the predictive data analysis computing entity 106 are performed by the breathing monitoring computing entity 101. In some of the noted embodiments, the breathing monitoring computing entity 101 is configured to receive observed breathing pattern sensory data from the breathing monitoring computing entity 101, process the observed breathing pattern sensory data to determine one or more prediction-based actions, and perform one or more prediction-based actions. In some embodiments, the predictive data analysis computing entity 106 may be configured to perform the one or more prediction-based actions by interacting with at least one of the breathing monitoring computing entity 101, client computing entity 102, and the external computing entities 103.

The breathing monitoring computing entity 101 may be configured to record breathing pattern sensory data for a monitored individual and to communicate the breathing pattern sensory data to at least one of the predictive data analysis computing entity 106, the client computing entity 102, and the external computing entities 103. In some embodiments, the breathing monitoring computing entity 101 is directly connected to the predictive data analysis computing entity 106. In some embodiments, the breathing monitoring computing entity 101 is configured to transmit the breathing pattern sensory data to the breathing monitoring computing entity 101, and the breathing monitoring computing entity 101 is configured to forward the breathing pattern sensory data received from the breathing monitoring computing entity 101 to the predictive data analysis computing entity 106. In some embodiments, the breathing monitoring computing entity 101 is configured to transmit the breathing pattern sensory data to the client computing entity 102, and the client computing entity 102 is configured to forward the breathing pattern sensory data received from the breathing monitoring computing entity 101 to the predictive data analysis computing entity 106. In some embodiments, the breathing monitoring computing entity 101 is configured to transmit the breathing pattern sensory data to the one or more external computing entities 103, and the one or more external computing entities 103 is configured to forward the breathing pattern sensory data received from the breathing monitoring computing entity 101 to the predictive data analysis computing entity 106.

In some embodiments, the breathing monitoring computing entity 101 includes one or more breathing sensors. In some embodiments, the breathing monitoring computing entity 101 includes a display that is configured to display a user interface. Such a user interface could include, for example, one or more of a display screen, an audio speaker, or a tactile output. In some embodiments, the user interface allows the user to communicate with the system. For example, in some embodiments, the system may include a keyboard, microphone, or touch screen allowing the user to enter information related to breathing pattern such as time, intensity of physical activity, stress level, energy level, location, environmental condition, and/or the like.

The client computing entity 102 may be configured to enable user display of the observed breathing pattern sensory data, the observed inspiration-expiration waveform pattern, the predicted interruption score, and/or user configuration of predictive management actions performed by the predictive data analysis computing entity 106. Examples of client computing entities 102 include smartphone devices, tablet devices, personal computer devices, and/or the like. The client computing entity 102 may include a short-range communication network receiver (e.g., a Bluetooth receiver) that is configured to receive observed breathing pattern sensory data from the breathing monitoring computing entity 101. The client computing entity 102 may further be configured to provide the observed breathing pattern sensory data received from the breathing monitoring computing entity 101 to the predictive data analysis computing entity 106 and/or to receive one or more therapeutic notifications from the predictive data analysis computing entity 106.

In some embodiments, the client computing entity 102 is configured to perform some or all of the functionalities of the predictive data analysis computing entity 106. In some of the noted embodiments, the client computing entity 102 is configured to receive breathing pattern sensory data from the breathing monitoring computing entity 101, process the breathing pattern sensory data to determine one or more prediction-based actions, and perform the one or more prediction-based actions. In some embodiments, the breathing monitoring computing entity 101 may be configured to perform the one or more prediction-based actions by interacting with at least one of the breathing monitoring computing entity 101, client computing entity 102, and the external computing entities 103.

The external computing entities 103 may be configured to receive notification data and/or user interface data generated by the predictive data analysis computing entity 106 and perform corresponding actions based at least in part on the received data. For example, an external computing entity 103 may be configured to generate one or more physician alerts and/or one or more healthcare provider alerts based at least in part on the notification data provided by the predictive data analysis computing entity 106. As another example, an external computing entity 103 may be configured to generate one or more automated physician appointments, automated medical notes, automated prescription recommendations, and/or the like based at least in part on the notification data received from the predictive data analysis computing entity 106. As yet another example, an external computing entity 103 may be configured to enable an end-user device associated with the external computing entity 103 to display a user interface, where the user interface may have been generated based at least in part on the user interface data provided by the predictive data analysis computing entity 106. Examples of external computing entities 103 include hospital servers, physician server, laboratory servers, emergency room servers, urgent care center servers, research institution servers, and/or the like.

Exemplary Predictive Data Analysis Computing Entity

FIG. 2 provides a schematic of a predictive data analysis computing entity 106 according to one embodiment of the present invention. In general, the terms computing entity, computer, entity, device, system, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the predictive data analysis computing entity 106 may also comprise one or more network interfaces 220 for communicating with various computing entities, such as by communicating data, content, information, and/or similar terms used herein interchangeably that can be transmitted, received, operated on, processed, displayed, stored, and/or the like.

As shown in FIG. 2, in one embodiment, the predictive data analysis computing entity 106 may comprise or be in communication with one or more processing elements 205 (also referred to as processors, processing circuitry, and/or similar terms used herein interchangeably) that communicate with other elements within the predictive data analysis computing entity 106 via a bus, for example. As will be understood, the processing element 205 may be embodied in a number of different ways.

For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, another circuitry, and/or the like.

As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the predictive data analysis computing entity 106 may further comprise or be in communication with non-volatile media (also referred to as non-volatile storage, memory, memory storage, memory circuitry and/or similar terms used herein interchangeably). In one embodiment, the non-volatile storage or memory may comprise one or more non-volatile storage or memory media 210, including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or information/data that is stored in a computer-readable storage medium using one or more database models, such as a hierarchical database model, network model, relational model, entity—relationship model, object model, document model, semantic model, graph model, and/or the like.

In one embodiment, the predictive data analysis computing entity 106 may further comprise or be in communication with volatile media (also referred to as volatile storage, memory, memory storage, memory circuitry and/or similar terms used herein interchangeably). In one embodiment, the volatile storage or memory may also comprise one or more volatile storage or memory media 215, including but not limited to RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like.

As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the predictive data analysis computing entity 106 with the assistance of the processing element 205 and operating system.

As indicated, in one embodiment, the predictive data analysis computing entity 106 may also comprise one or more communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the predictive data analysis computing entity 106 may be configured to communicate via wireless client communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

Although not shown, the predictive data analysis computing entity 106 may comprise or be in communication with one or more input elements, such as a keyboard input, a mouse input, a touch screen/display input, motion input, movement input, audio input, pointing device input, joystick input, keypad input, and/or the like. The predictive data analysis computing entity 106 may also comprise or be in communication with one or more output elements (not shown), such as audio output, video output, screen/display output, motion output, movement output, and/or the like.

Exemplary Breathing Monitoring Computing Entity

FIG. 3 provides an illustrative schematic representative of a breathing monitoring computing entity 101 that can be used in conjunction with embodiments of the present invention. In general, the terms device, system, computing entity, entity, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Breathing monitoring computing entities 101 can be operated by various parties. As shown in FIG. 3, the breathing monitoring computing entity 101 can comprise an antenna 312, a transmitter 304 (e.g., radio), a receiver 306 (e.g., radio), a processing element 308 (e.g., CPLDs, microprocessors, multi-core processors, coprocessing entities, ASIPs, microcontrollers, and/or controllers) that provides signals to and receives signals from the transmitter 304 and receiver 306, correspondingly, a power source 326, and a breathing sensor 328.

As noted above, in some embodiments, the breathing monitoring computing entity 101 may include one or more breathing sensors (such as breathing sensor 328). In some embodiments the one or more breathing sensors are incorporated in a wearable device. In various embodiments, the one or more breathing sensors are coupled and/or secured to and/or integrated into the wearable device. In some embodiments, the one or more breathing sensors are arranged over a particular area of the wearable device, such as an area expected to cover one or more target organs (e.g., diaphragm, heart, and/or lungs). For example, in some embodiments, the one or more breathing sensors comprise a stretch sensor configured to be positioned with respect to the diaphragm of the monitored individual to measure the inspiration and expiration pattern of the monitored individual as the diaphragm of the monitored individual contracts and expands as the monitored individual breathes. In some embodiments, the breathing monitoring computing entity 101 may be configured to record the inspiration and expiration pattern measured by the stretch sensor. The monitored inspiration and expiration pattern may be represented as a breathing pattern sensory data.

The signals provided to and received from the transmitter 304 and the receiver 306, correspondingly, may comprise signaling information/data in accordance with air interface standards of applicable wireless systems. In this regard, the breathing monitoring computing entity 101 may be capable of operating with one or more air interface standards, communication protocols, modulation types, and access types. More particularly, the breathing monitoring computing entity 101 may operate in accordance with any of a number of wireless communication standards and protocols, such as those described above with regard to the predictive data analysis computing entity 106. In a particular embodiment, the breathing monitoring computing entity 101 may operate in accordance with multiple wireless communication standards and protocols, such as UMTS, CDMA2000, 1×RTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the breathing monitoring computing entity 101 may operate in accordance with multiple wired communication standards and protocols, such as those described above with regard to the predictive data analysis computing entity 106 via a network interface 320.

Via these communication standards and protocols, the breathing monitoring computing entity 101 can communicate with various other entities using concepts such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The breathing monitoring computing entity 101 can also download changes, add-ons, and updates, for instance, to its firmware, software (e.g., including executable instructions, applications, program modules), and operating system.

According to one embodiment, the breathing monitoring computing entity 101 may comprise location determining aspects, devices, modules, functionalities, and/or similar words used herein interchangeably. For example, the breathing monitoring computing entity 101 may comprise outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This information/data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data can be determined by triangulating the breathing monitoring computing entity's 101 position in connection with a variety of other systems, including cellular towers, Wi-Fi access points, and/or the like. Similarly, the breathing monitoring computing entity 101 may comprise indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may comprise the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

In some embodiments, the transmitter 304 may include one or more Bluetooth transmitters. In some embodiments, the receiver 306 may include one or more Bluetooth receivers. The Bluetooth transmitters and/or the Bluetooth receivers may be configured to communicate with at least one of the client computing entity 102 and the predictive data analysis computing entity 106. In some embodiments, the transmitter 304 may include one or more WAN transmitters.

In some embodiments, the receiver 306 may include one or more WAN receivers. The WAN transmitters and/or the WAN receivers may be configured to communicate with at least one of the client computing entity 102, the external computing entities 103, and the predictive data analysis computing entity 106.

The power source 326 may include electric circuitry configured to enable powering the breathing monitoring computing entity 101. The power source 326 may include one or more batteries, such as a rechargeable lithium-ion (Li-Ion) battery, that are configured to act as sources of electric power for the breathing monitoring computing entity 101.

The breathing monitoring computing entity 101 may also comprise a user interface (that can optionally comprise a display 316 coupled to a processing element 308) and/or a user input interface (coupled to a processing element 308). For example, the user interface may be a user application, browser, user interface, and/or similar words used herein interchangeably executing on and/or accessible via the breathing monitoring computing entity 101 to interact with and/or cause display of information/data from the predictive data analysis computing entity 106, as described herein. The user input interface can comprise any of a number of devices or interfaces allowing the breathing monitoring computing entity 101 to receive data, such as a keypad 318 (hard or soft), a touch display, voice/speech or motion interfaces, or other input device. In embodiments including a keypad 318, the keypad 318 can comprise (or cause display of) the conventional numeric (0-9) and related keys (#, *), and other keys used for operating the breathing monitoring computing entity 101 and may comprise a full set of alphabetic keys or set of keys that may be activated to provide a full set of alphanumeric keys. In addition to providing input, the user input interface can be used, for example, to activate or deactivate certain functions, such as screen savers and/or sleep modes.

The breathing monitoring computing entity 101 can also comprise volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the breathing monitoring computing entity 101. As indicated, this may comprise a user application that is resident on the entity or accessible through a browser or other user interface for communicating with the predictive data analysis computing entity 106 and/or various other computing entities.

In another embodiment, the breathing monitoring computing entity 101 may comprise one or more components or functionalities that are the same or similar to those of the predictive data analysis computing entity 106, as described in greater detail above. As will be recognized, these architectures and descriptions are provided for exemplary purposes only and are not limiting to the various embodiments.

Exemplary Client Computing Entity

FIG. 4 provides an illustrative schematic representative of a client computing entity 102 that can be used in conjunction with embodiments of the present invention. In general, the terms device, system, computing entity, entity, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Client computing entities 102 can be operated by various parties. As shown in FIG. 4, the client computing entity 102 can comprise an antenna 412, a transmitter 404 (e.g., radio), a receiver 406 (e.g., radio), a processing element 408 (e.g., CPLDs, microprocessors, multi-core processors, coprocessing entities, ASIPs, microcontrollers, and/or controllers) that provides signals to and receives signals from the transmitter 404 and receiver 406, correspondingly, and a power source 426.

The signals provided to and received from the transmitter 404 and the receiver 406, correspondingly, may comprise signaling information/data in accordance with air interface standards of applicable wireless systems. In this regard, the client computing entity 102 may be capable of operating with one or more air interface standards, communication protocols, modulation types, and access types. More particularly, the client computing entity 102 may operate in accordance with any number of wireless communication standards and protocols, such as those described above with regard to the predictive data analysis computing entity 106. In a particular embodiment, the client computing entity 102 may operate in accordance with multiple wireless communication standards and protocols, such as UMTS, CDMA2000, 1×RTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the client computing entity 102 may operate in accordance with multiple wired communication standards and protocols, such as those described above with regard to the predictive data analysis computing entity 106 via a network interface 420.

Via these communication standards and protocols, the client computing entity 102 can communicate with various other entities using concepts such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The client computing entity 102 can also download changes, add-ons, and updates, for instance, to its firmware, software (e.g., including executable instructions, applications, program modules), and operating system.

According to one embodiment, the client computing entity 102 may comprise location determining aspects, devices, modules, functionalities, and/or similar words used herein interchangeably. For example, the client computing entity 102 may comprise outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This information/data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data can be determined by triangulating the client computing entity's 102 position in connection with a variety of other systems, including cellular towers, Wi-Fi access points, and/or the like. Similarly, the client computing entity 102 may comprise indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may comprise the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

In some embodiments, the transmitter 404 may include one or more Bluetooth transmitters. In some embodiments, the receiver 406 may include one or more Bluetooth receivers. The Bluetooth transmitters and/or the Bluetooth receivers may be configured to communicate with the breathing monitoring computing entity 101. In some embodiments, the transmitter 404 may include one or more WAN transmitters. In some embodiments, the receiver 406 may include one or more WAN receivers. The WAN transmitters and/or the WAN receivers may be configured to communicate with the predictive data analysis computing entity 106.

The power source 426 may include electric circuitry configured to enable powering the client computing entity 102. The power source 426 may include one or more batteries, such as a nickel metal-hydride (NiMH) battery, that are configured to act as sources of electric power for the client computing entity 102.

The client computing entity 102 may also comprise a user interface (that can comprise a display 416 coupled to a processing element 408) and/or a user input interface (coupled to a processing element 408). For example, the user interface may be a user application, browser, user interface, and/or similar words used herein interchangeably executing on and/or accessible via the client computing entity 102 to interact with and/or cause display of information/data from the predictive data analysis computing entity 106, as described herein. The user input interface can comprise any of a number of devices or interfaces allowing the client computing entity 102 to receive data, such as a keypad 418 (hard or soft), a touch display, voice/speech or motion interfaces, or other input device. In embodiments including a keypad 418, the keypad 418 can comprise (or cause display of) the conventional numeric (0-9) and related keys (#, *), and other keys used for operating the client computing entity 102 and may comprise a full set of alphabetic keys or set of keys that may be activated to provide a full set of alphanumeric keys. In addition to providing input, the user input interface can be used, for example, to activate or deactivate certain functions, such as screen savers and/or sleep modes.

The client computing entity 102 can also comprise volatile storage or memory 422 and/or non-volatile storage or memory 424, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the client computing entity 102. As indicated, this may comprise a user application that is resident on the entity or accessible through a browser or other user interface for communicating with the predictive data analysis computing entity 106 and/or various other computing entities.

In another embodiment, the client computing entity 102 may comprise one or more components or functionalities that are the same or similar to those of the predictive data analysis computing entity 106, as described in greater detail above. As will be recognized, these architectures and descriptions are provided for exemplary purposes only and are not limiting to the various embodiments.

Exemplary External Computing Entity

FIG. 5 provides a schematic of an external computing entity 103 according to one embodiment of the present invention. In general, the terms computing entity, computer, entity, device, system, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the predictive data analysis computing entity 106 may also comprise one or more network interfaces 520 for communicating with various computing entities, such as by communicating data, content, information, and/or similar terms used herein interchangeably that can be transmitted, received, operated on, processed, displayed, stored, and/or the like.

As shown in FIG. 5, in one embodiment, the external computing entity 103 may comprise or be in communication with one or more processing elements 505 (also referred to as processors, processing circuitry, and/or similar terms used herein interchangeably) that communicate with other elements within the external computing entity 103 via a bus, for example. As will be understood, the processing element 505 may be embodied in a number of different ways.

For example, the processing element 505 may be embodied as one or more complex programmable logic devices (CPLDs), microprocessors, multi-core processors, coprocessing entities, application-specific instruction-set processors (ASIPs), microcontrollers, and/or controllers. Further, the processing element 505 may be embodied as one or more other processing devices or circuitry. The term circuitry may refer to an entirely hardware embodiment or a combination of hardware and computer program products. Thus, the processing element 505 may be embodied as integrated circuits, application specific integrated circuits (ASICs), field programmable gate arrays (FPGAs), programmable logic arrays (PLAs), hardware accelerators, another circuitry, and/or the like.

As will therefore be understood, the processing element 505 may be configured for a particular use or configured to execute instructions stored in volatile or non-volatile media or otherwise accessible to the processing element 505. As such, whether configured by hardware or computer program products, or by a combination thereof, the processing element 505 may be capable of performing steps or operations according to embodiments of the present invention when configured accordingly.

In one embodiment, the external computing entity 103 may further comprise or be in communication with non-volatile media (also referred to as non-volatile storage, memory, memory storage, memory circuitry and/or similar terms used herein interchangeably). In one embodiment, the non-volatile storage or memory may comprise one or more non-volatile storage or memory media 510, including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or information/data that is stored in a computer-readable storage medium using one or more database models, such as a hierarchical database model, network model, relational model, entity—relationship model, object model, document model, semantic model, graph model, and/or the like.

In one embodiment, the external computing entity 103 may further comprise or be in communication with volatile media (also referred to as volatile storage, memory, memory storage, memory circuitry and/or similar terms used herein interchangeably). In one embodiment, the volatile storage or memory may also comprise one or more volatile storage or memory media 515, including but not limited to RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like.

As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 505. Thus, the databases, database instances, database management systems, data, applications, programs, program modules, scripts, source code, object code, byte code, compiled code, interpreted code, machine code, executable instructions, and/or the like may be used to control certain aspects of the operation of the predictive data analysis computing entity 106 with the assistance of the processing element 505 and operating system.

As indicated, in one embodiment, the external computing entity 103 may also comprise one or more network interfaces 520 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the predictive data analysis computing entity 106 may be configured to communicate via wireless client communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

Although not shown, the predictive data analysis computing entity 106 may comprise or be in communication with one or more input elements, such as a keyboard input, a mouse input, a touch screen/display input, motion input, movement input, audio input, pointing device input, joystick input, keypad input, and/or the like. The predictive data analysis computing entity 106 may also comprise or be in communication with one or more output elements (not shown), such as audio output, video output, screen/display output, motion output, movement output, and/or the like.

V. EXEMPLARY METHOD OPERATIONS

As described below, various embodiments of the present invention address technical challenges related to efficiently and effectively performing splinting activity detection based at least in part on observed breathing pattern sensory data for a monitored individual. The disclosed techniques improve the efficiency and effectiveness of splinting activity detection by utilizing a splinting activity detection machine learning model that is configured to compare an observed inspiration-expiration waveform pattern that is generated based at least in part on observed breathing pattern sensory data with the one or more expected inspiration-expiration waveform patterns. The splinting activity detection machine learning models utilize comparison operations that may, in at least some embodiments, reduce or eliminate the need for computationally expensive training operations in order to generate the noted splinting activity detection machine learning models.

By reducing or eliminating the noted training operations, various embodiments of the present invention: (i) reduces or eliminates the computational operations needed for training and thus improves the computational efficiency of performing splinting activity detection, (ii) reduces or eliminates the need for storage resources to train/generate splinting activity detection machine learning models and thus improves storage efficiency of performing splinting activity detection, and (iii) reduces or eliminates the need for transmitting extensive training data needed to generate splinting activity detection machine learning models and thus improves transmission/network efficiency of performing splinting activity detection. Via the noted advantages, various embodiments of the present invention make substantial technical contributions to the fields of splinting activity detection in particular and healthcare-related predictive data analysis in general.

FIG. 6 is a flowchart diagram of an example process for performing a machine-learning-based splinting activity detection, in accordance with some embodiments discussed herein. Via the various steps/operations of the process 600, the predictive data analysis computing entity 106 can relate a predicted interruption score generated based at least in part on an observed inspiration-expiration waveform pattern and one or more expected inspiration-expiration waveform patterns to splinting activity detection.

The process 600 begins at step/operation 601 when the predictive data analysis computing entity 106 identifies observed breathing pattern sensory data. The observed breathing sensory data may describe breathing measurements for a monitored individual with respect to whom the predictive data analysis computing entity 106 seeks to obtain one or more recommended prediction-based actions. The observed breathing pattern sensory data may describe breathing measurements associated with a corresponding breathing cycle (e.g., inspiration-expiration cycle). For example, in some embodiments, the observed breathing sensory data may comprise an observed breathing sensory timeseries data object that describes recorded breathing measurements for the monitored individual over an inspiration-expiration cycle of the monitored individual. In some embodiments, the breathing measurements may include voltage signals and/or the like associated with inspiration and/or expiration.

In some embodiments, the observed breathing pattern sensory data may be calculated using one or more breathing sensors. For example, the breathing sensors may be configured to record breathing measurements for the monitored individual and to transmit (e.g., wirelessly, through a wired transmission medium, and/or the like) the recorded breathing measurements to one or more computing entities (e.g., the predictive data analysis computing entity 106, the breathing monitoring computing entity 101, the client computing entity 102, and/or the external computing entities 103) configured to store the breathing measurements and/or determine an observed inspiration-expiration waveform pattern based at least in part on the breathing measurements.

In some embodiments, the breathing sensors may include breathing sensors that are in direct contact with the monitored individual's body as well as breathing sensors that are not in direct contact with the monitored individual's body. For example, in some embodiments, the one or more breathing sensors may be integrated and/or secured to a wearable device (e.g., vest, shirt, body band, and/or the like.). In example embodiments, the one or more breathing sensors may include one or more stretch sensors integrated and/or secured to a stretchable wearable device positioned with respect to one or more target organs (e.g., diaphragm) of the monitored individual. In such embodiments, the stretch sensors may be configured to measure the contraction of the diaphragm and/or expansion of the diaphragm of the monitored individual as the monitored individual inspires and expires. For example, in some embodiments, the breathing pattern sensory data may comprise a first sensory indicator of a diaphragm expansion for the monitored individual and a second indicator of a diaphragm contraction for the monitored individual.

In some embodiments, the observed breathing pattern sensory data may be associated with an activity period designation of one or more activity period designations and/or an activity severity level of one or more activity severity levels. For example, an activity period designation for particular observed breathing pattern sensory may describe that the particular observed breathing pattern sensory data is associated with running, breathing, resting, sleeping, and/or the like. As another example, an activity severity level for particular observed breathing pattern sensory data may describe that the particular observed breathing pattern sensory data is associated with a high level of activity severity, a low level of activity severity, a medium level of activity severity, etc. In some embodiments, each activity period designation and/or each activity severity level may be determined based at least in part on user input. For example, the user input may be a user input related to one or more user activity events (e.g., type of activity, intensity of activity, energy level, altitude, and/or the like). In some embodiments, the user input may be received via a user interface of the client computing entity 102 (e.g., a user interface of the breathing monitoring computing entity 101, a user interface of the client computing entity 102, and/or the like).

In some embodiments, each activity period designation and/or each activity severity level may be determined based at least in part on biometric data (e.g., heart rate data, pulse data, and/or the like). For example, the observed breathing sensory data may be observed breathing sensory timeseries data object that temporally aligns with a biometric timeseries data object that describes a biometric data. In some embodiments, the observed breathing sensory timeseries data object and the biometric timeseries data object are deemed to temporally align if at least n (e.g., at least one, or at least a required ratio of) of the corresponding time windows described by the observed breathing sensory timeseries data object and the biometric timeseries data object refer to common periods. For example, in some embodiments, a given observed breathing sensory data object that includes n observed breathing sensory time windows and a biometric timeseries data object that includes m biometric timeseries windows, and given that p of the n observed breathing sensory time windows correspond to time periods described by the m biometric time windows, the observed breathing sensory timeseries data object and the biometric timeseries data object may in some embodiments be deemed to align if p satisfies a temporal alignment threshold.

As another example, in some embodiments, given an observed breathing sensory timeseries data object that includes n observed breathing time windows and a biometric timeseries data object that includes m biometric time windows, and given that p of the m biometric time windows correspond to time periods described by the n observed breathing sensory time windows, the breathing sensory timeseries data object and the biometric timeseries data object may in some embodiments be deemed to align if p satisfies a temporal alignment threshold. As yet another example, in some embodiments, given an observed breathing sensory timeseries data object that includes n observed breathing sensory time windows and a biometric timeseries data object that includes m biometric time windows, and given that p of the n observed breathing sensory time windows correspond to time periods described by the m biometric time windows, and further given that q of the m biometric time windows correspond to time periods described by the n observed breathing time windows, the breathing timeseries data object and the biometric timeseries data object may in some embodiments be deemed to align if p satisfies a first temporal alignment threshold and q satisfies a second temporal alignment threshold.

At step/operation 602, the predictive data analysis computing entity 106 determines an observed inspiration-expiration waveform pattern based at least in part on the observed breathing pattern sensory data. The observed inspiration-expiration waveform pattern may describe the inspiration pattern and/or expiration pattern of the observed breathing pattern sensory data corresponding to a particular inspiration-expiration cycle.

Operational examples of observed inspiration-expiration waveform patterns are depicted in FIGS. 7 and 8. FIG. 7 depicts an observed inspiration-expiration waveform pattern 700 for a first observed breathing pattern sensory data. FIG. 8 depicts another observed inspiration-expiration waveform pattern 800 for a second breathing pattern sensory data. As shown in FIGS. 7 and 8, an observed inspiration-expiration waveform pattern may represent a substantially triangular pattern. The substantially triangular inspiration-expiration waveform pattern may comprise a left half-triangular pattern that is associated with a detected inspiration pattern for the observed breathing pattern sensory data. For example, the left-half triangular pattern may describe a positive slope (e.g., upward progression) that corresponds to the inspiration pattern for the observed breathing pattern sensory data of a monitored individual. Additionally, the substantially triangular inspiration-expiration waveform pattern may comprise a right half triangular pattern that is associated with a detected expiration pattern for the observed breathing pattern sensory data. For example, the right half triangular pattern may describe a negative slope that corresponds to the expiration pattern for the observed breathing pattern sensory data of a monitored individual.

As depicted in FIGS. 7 and 8, a particular observed inspiration-expiration waveform pattern may describe one or more attributes of the corresponding observed breathing pattern sensory data. For example, a particular observed inspiration-expiration waveform pattern may describe a peak inspiration (e.g., the maximum point in the upward progression of the left half triangular pattern) of the corresponding observed breathing pattern sensory data. For instance, the peak inspiration of the observed inspiration-expiration waveform pattern depicted in FIG. 7. is X and the peak inspiration of the observed inspiration-expiration waveform pattern depicted in FIG. 8 is Y.

As another example, the observed inspiration-expiration waveform pattern may describe a time from the beginning of the observed inspiration-expiration waveform pattern to a peak inspiration of the observed inspiration-expiration waveform pattern. For instance, the time from the beginning of the observed inspiration-expiration waveform pattern to a peak inspiration of the observed inspiration-expiration waveform pattern depicted in FIG. 7. is about 3 seconds and the time from the beginning of the observed inspiration-expiration waveform pattern to a peak inspiration of the observed inspiration-expiration waveform pattern depicted in FIG. 8 is about 1.2 seconds.

As another example, the observed inspiration-expiration waveform pattern may describe a time from the peak inspiration of the observed inspiration-expiration waveform pattern to the end of the observed inspiration-expiration waveform pattern. As yet another example, the inspiration-expiration waveform pattern may describe a time from the beginning of the observed inspiration-expiration waveform pattern to the end of the observed inspiration-expiration waveform pattern. As yet another example, the observed inspiration-expiration waveform pattern may describe one or more interruptions in the progression of observed inspiration-expiration waveform pattern. For instance, as depicted in FIG. 7, the observed inspiration-expiration waveform describes abrupt interruption 702 in the upward progression of the left half triangular pattern.

Returning to FIG. 6, at step/operation 603, the predictive data analysis computing entity 106 utilizes a splinting activity detection machine learning model to generate a predicted interruption score for the observed breathing pattern sensory data based at least in part on the observed inspiration-expiration waveform pattern and one or more expected inspiration-expiration waveform patterns. In some embodiments, the splinting activity detection machine learning model may describe a plurality of expected inspiration-expiration waveform patterns. In some embodiments, the plurality of expected inspiration-expiration waveform patterns may comprise one or more periodic subsets of the plurality of expected inspiration-expiration waveform patterns. Each periodic subset may be associated with an activity period designation of one or more activity period designation and/or an activity severity level of one or more activity severity levels. Additionally or alternatively, in some embodiments, the plurality of expected inspiration-expiration waveform patterns may comprise one or more activity severity subsets of the plurality of expected inspiration-expiration waveform patterns. Each activity severity subset may be associated with an activity severity level of one or more activity severity levels.

In some embodiments, the one or more expected inspiration-expiration waveform pattern may be selected from the one or more periodic subsets of the plurality of expected inspiration-expiration waveform patterns based at least in part on a target activity period designation for the observed breathing pattern sensory data. Additionally or alternatively, in some embodiments, the one or more expected inspiration-expiration waveform patterns may be selected from the one or more activity severity subsets of the plurality of expected inspiration-expiration waveform patterns based at least in part on a target activity severity level for the observed breathing pattern sensory data. In some embodiments, the target activity period designation and/or the target activity severity level may be determined based at least in part on biometric data associated with the breathing pattern sensory data.

An operational example of an expected inspiration-expiration waveform pattern is depicted in FIG. 9. As shown in FIGS. 9, the expected inspiration-expiration waveform pattern 900 may represent a substantially triangular pattern. The substantially triangular expected inspiration-expiration waveform pattern may comprise a left half-triangular pattern that is associated with an inspiration pattern of an expected breathing pattern sensory data. For example, the left-half triangular pattern may describe a positive slope (e.g., upward progression) that corresponds to the inspiration pattern of an expected breathing pattern sensory data for a monitored individual. Additionally, the substantially triangular inspiration-expiration waveform pattern may comprise a right half triangular pattern that is associated with a detected expiration pattern of an expected breathing pattern sensory data. For example, the right half triangular pattern may describe a negative slope that corresponds to the expiration pattern of an expected breathing pattern data for the monitored individual.

As depicted in FIG. 9, the expected inspiration-expiration waveform pattern may describe one or more attributes of the corresponding expected breathing pattern sensory data. For example, the expected inspiration-expiration waveform pattern may describe a peak inspiration (e.g., the maximum point in the upward progression of the left half triangular pattern) of the corresponding expected breathing pattern sensory data. For instance, the peak inspiration of the expected inspiration-expiration waveform pattern depicted in FIG. 9. is Z.

As another example, the expected inspiration-expiration waveform pattern may describe a time from the beginning of the expected inspiration-expiration waveform pattern to a peak inspiration of the expected inspiration-expiration waveform pattern. For instance, the time from the beginning of the expected inspiration-expiration waveform pattern to a peak inspiration of the expected inspiration-expiration waveform pattern depicted in FIG. 9 is about 2 seconds.

As another example, the expected inspiration-expiration waveform pattern may describe a time from the peak inspiration of the expected inspiration-expiration waveform pattern to the end of the expected inspiration-expiration waveform pattern. As yet another example, the expected inspiration-expiration waveform pattern may describe a time from the beginning of the expected inspiration-expiration waveform pattern to the end of the expected inspiration-expiration waveform pattern. As yet another example, the expected inspiration-expiration waveform pattern may describe one or more expected interruptions in the progression of the expected inspiration-expiration waveform pattern.

Returning to FIG. 6, in some embodiments, the predicted interruption score is generated based at least in part by comparing the observed inspiration-expiration waveform pattern with the one or more expected inspiration-expiration waveform patterns and determining one or more difference measures for the observed inspiration-expiration waveform pattern and the one or more inspiration-expiration waveform patterns. In some embodiments, the step/operation 603 may be performed in accordance with the process that is depicted in FIG. 10, which is an example process for determining an interruption score based at least in part on comparing an observed inspiration-expiration waveform pattern to a particular inspiration expiration waveform pattern of the one or more expected inspiration-expiration waveform patterns.

The process that is depicted in FIG. 10 begins at step/operation 1001 when the predictive data analysis computing entity 106 determines one or more attributes of the observed inspiration-expiration waveform pattern. The process continues at step/operation 1002, when the predictive data analysis computing entity 106 determines one or more attributes of the particular expected inspiration-expiration waveform patterns. At step/operation 1003, the predictive data analysis computing entity 106 compares the one or more attributes of the observed inspiration-expiration waveform pattern to the one or more attributes of the particular expected inspiration-expiration waveform pattern and determines a difference measure for the observed inspiration-expiration waveform pattern and the particular inspiration-expiration waveform pattern.

For example, in some embodiments, when comparing an observed inspiration-expiration waveform pattern to a particular expected inspiration-expiration waveform pattern of the one or more expected inspiration-expiration waveform patterns, the predictive data analysis computing entity 106 compares a peak inspiration of the observed inspiration-expiration waveform pattern (e.g., observed peak inspiration) to a peak inspiration of the particular expected inspiration-expiration waveform pattern (e.g., expected peak inspiration) and determines a difference measure for the observed inspiration-expiration waveform pattern and the particular expected inspiration-expiration waveform pattern.

As another example, in some embodiments, when comparing an observed inspiration-expiration waveform pattern to a particular expected inspiration-expiration waveform pattern, the predictive data analysis computing entity 106 compares a time from the beginning of the observed inspiration-expiration waveform pattern to a peak inspiration of the observed inspiration-expiration waveform pattern to a time from the beginning of the particular expected inspiration-expiration waveform pattern to a peak inspiration of the expected inspiration-expiration waveform pattern and determines a difference measure between the times for the observed inspiration-expiration waveform pattern and the particular expected inspiration-expiration waveform pattern.

As yet another example, in some embodiments, when comparing an observed inspiration-expiration waveform pattern to a particular expected inspiration-expiration waveform pattern, the predictive data analysis computing entity 106 compares a ratio of time from the beginning of the observed inspiration-expiration waveform pattern to a peak inspiration of the observed inspiration-expiration waveform pattern to a ratio of time from the beginning of the particular expected inspiration-expiration waveform pattern to a peak inspiration of the expected inspiration-expiration waveform pattern and determines a difference measure between the two ratios for the observed inspiration-expiration waveform pattern and the particular expected inspiration-expiration waveform pattern.

As yet another example, in some embodiments, when comparing an observed inspiration-expiration waveform pattern to a particular expected inspiration-expiration waveform pattern, the predictive data analysis computing entity 106 compares one or more of (i) an observed peak inspiration of the observed inspiration-expiration waveform pattern to an expected peak inspiration of the particular expected inspiration-expiration waveform pattern, (ii) a time from the beginning of the observed inspiration-expiration waveform pattern to a peak inspiration of the observed inspiration-expiration waveform pattern to a time from the beginning of the particular expected inspiration-expiration waveform pattern to a peak inspiration of the expected inspiration-expiration waveform pattern, and (iii) a ratio of time from the beginning of the observed inspiration-expiration waveform pattern to a peak inspiration of the observed inspiration-expiration waveform pattern to a ratio of time from the beginning of the particular expected inspiration-expiration waveform pattern to a peak inspiration of the expected inspiration-expiration waveform pattern.

In some embodiments, the predictive data analysis computing entity determines the predicted interruption score based at least in part on whether a lowest difference measure associated with the observed inspiration-expiration waveform pattern satisfies a difference measure threshold. In some embodiments, the predictive data analysis computing entity 106 in response to determining that the predicted interruption score satisfies a predicted interruption score threshold, classifies, the observed inspiration-expiration waveform pattern as a splinting pattern. In some embodiments, the predictive data analysis computing entity determines a splinting severity level associated with the observed inspiration-expiration waveform pattern.

For example, in some embodiments, the predictive data analysis determines the splinting severity level associated with the observed inspiration-expiration by detecting an interruption in the progression (e.g., upward progression of the left hand triangular pattern) of the observed inspiration-expiration waveform pattern, determining the interruption duration (e.g., duration of the interruption) and determining the splinting severity level based at least in part on the interruption duration. For example in some embodiments, an interruption duration of 50 ms may correspond to a splinting severity level of 1 and an interruption of 100 ms correspond to a splinting severity level of 2. In the noted example, a longer interruption duration correspond to a higher splinting severity level. As another example, in some embodiments, an abrupt stop in the upward progression of the observed inspiration-expiration waveform pattern may correspond to a severity level of 5. Additionally or alternatively, in some embodiments, the predicted interruption score may be determined based at least in part on the severity level. Additionally or alternatively, in some embodiments, generating the predicted interruption score includes receiving biometric data (e.g., heart rate data, blood pressure data, glucose level data, adrenaline level data, and/or the like) associated with the monitored individual and generating the interruption score based at least in part on the received biometric data. In some embodiments, the biometric data may be received from devices such as a smart watch, IoT device, and/or the like.

In some embodiments, the splint activity detection machine learning models utilize comparison operations that may, in at least some embodiments, reduce or eliminate the need for computationally expensive training operations in order to generate the noted splinting activity detection machine learning models. By reducing or eliminating the noted training operations, various embodiments of the present invention: (i) reduces or eliminates the computational operations needed for training and thus improves the computational efficiency of performing splinting activity detection, (ii) reduces or eliminates the need for storage resources to train/generate splinting activity detection machine learning models and thus improves storage efficiency of performing splinting activity detection, and (iii) reduces or eliminates the need for transmitting extensive training data needed to generate splinting activity detection machine learning models and thus improves transmission/network efficiency of performing splinting activity detection. Via the noted advantages, various embodiments of the present invention make substantial technical contributions to the fields of splinting activity detection in particular and healthcare-related predictive data analysis in general.

Returning to FIG. 4, at step/operation 604, the predictive data analysis computing entity 106 performs one or more prediction based actions based at least in part on the predicted interruption score. For example, the predictive data analysis computing entity 106 may be configured to generate one or more physician alerts and/or one or more healthcare alerts based at least in part on the predicted interruption score and/or splinting severity level. As another example, the predictive data analysis computing entity 106 may be configured to generate one or more automated physician appointments, automated medical notes, automated prescription medications, automated physician instruction, and/or the like based at least in part on the predicted interruption score and/or splinting severity level. As another example, the predictive data analysis computing entity 106 may be configured to perform a therapeutic intervention, such as a therapy guided session based at least in part on the predicted interruption score and/or splinting severity level. For instance, in some embodiments, based at least on the predicted interruption score and/or splinting severity level, the predictive data analysis computing entity 106 may suggest one or more micro-interventions to the user, such as inspiring one second longer, inspiring faster, and/or the like. In some embodiments, the predictive data analysis computing entity 106 may be configured to suggest recommended actions (e.g., treatment, intervention, and/or the like) to the monitored individual's physician.

In some embodiments, the predictive data analysis computing entity may be configured to generate user interface data for display using a display device of a computing entity (e.g., the client computing entity 102). For example, in some embodiments, performing the one or more prediction-based actions comprises determining whether a splinting severity level associated with the monitored individual satisfies a splinting severity level threshold. Additionally, in response to determining that the splinting severity level satisfies the splinting severity level threshold, the predictive data analysis computing entity 106 generates user interface data for one or more therapeutic notifications corresponding to the observed inspiration-expiration waveform pattern. The one or more therapeutic notifications may be configured to be displayed using a display device of a computing entity (e.g., the client computing entity 102) associated with the monitored individual.

FIG. 11 provides an example user interface 1100 depicting one or more therapeutic notifications, in accordance with some embodiments discussed herein. As depicted in FIG. 11, examples of therapeutic notifications may include automated instructions based at least in part on the predicted interruption score and/or severity level, instructions received from a physician (e.g., via the external computing entities 103), instructions received from a healthcare provider, and/or the like. In some embodiments, the predictive data analysis computing entity may be configured to receive user inputs (e.g., input from a monitored individual during a therapeutic intervention). In some embodiments, the predictive data analysis computing entity 106 may be configured to enable an end-user to display a user interface where the user interface has been generated based at least in part on the predicted interruption score and/or splinting severity level.

As noted above, in some embodiments the predictive data analysis computing entity may be configured to perform a therapeutic intervention, such as a therapy guided session. In some embodiments, performing the therapeutic intervention comprise, in response to determining that the predicted interruption score satisfies a predicted interruption score threshold, the predictive data analysis computing entity 106 transmits a request to the monitored individual to perform a therapy guided session.

In some embodiments, as depicted in FIG. 11, the predictive data analysis computing entity 106 may display, using the display device of a computing entity (e.g., the client computing entity 102), the observed inspiration-expiration waveform pattern (e.g., in real time). For example, in some embodiments, the predictive data analysis computing entity 106 may display one or more observed inspiration-expiration waveform patterns corresponding to one or more observed breathing sensory data for the monitored individual during the therapy guided session. In some embodiments, the predictive data analysis computing entity 106 may display one or more user interface on the display device indicating key points associated with the one or more observed inspiration-expiration waveform patterns. For example, abrupt interruptions in the upward progression of the inspiration waveform pattern may be displayed in a particular color different from other portions of the inspiration-expiration waveform pattern. As noted above, in some embodiments, the predictive data analysis computing entity 106 may transmit therapeutic notifications via the display device to the monitored individual. For example, the predictive data analysis computing entity 106 may display user interface data that describes slow inspiration, fast inspiration, and/or the like of the corresponding observed inspiration-expiration waveform pattern on the display device. In some embodiments, the therapy guided session may continue until the predicted interruption score for an observed inspiration-expiration waveform pattern corresponding to an observed breathing pattern sensory data for the monitored individual fails to satisfy the predicted interruption score threshold. In some embodiments the therapy guided session may be configurable. For example, the monitored individual's physician may set limits (e.g., goals) for the monitored individual for a therapy guided session. In the noted example, different limits may be set for different (e.g., subsequent) therapy guided sessions.

In some embodiments, performing the one or more prediction-based actions (e.g., therapy guided session) comprise determining based at least in part on one or more predicted interruption scores and one or more severity levels for one or more observed breathing pattern sensory data recommended predicted actions for the monitored individual associated with the one or more predicted interruption scores and/or the one or more splinting severity levels for a prediction window. A prediction window may describe a period of time whose respective one or more predicted interruption scores and/or one or more splinting severity levels for one or more breathing pattern sensory data may be used to determine appropriate prediction-based actions to perform during an intervention window subsequent to the prediction window. For example, in some embodiments, a prediction window subset may describe a particular period of time prior to a current time, where the one or more predicted interruption scores and/or one or more splinting severity levels for the breathing pattern sensory data for the noted particular period of time may be used to determine appropriate prediction-based actions to perform during a subsequent period of time after the current time.

In some embodiments, the desired length of a period of time described by a prediction window is determined based at least in part on predefined configuration data, where the predefined configuration data may in turn be determined prior to runtime using user-provided (e.g., system administration data), using rule-based models configured to determine optimal prediction window lengths based at least in part on breathing measurement data for the prediction window and/or based at least in part on user activity data for the prediction window, using machine learning models configured to determine optical prediction window lengths, and/or the like. In some embodiments, the desired length of a period of time described by a prediction window is determined based at least in part on configuration data that are dynamically generated at run-time using user-provide data (e.g., system administration data), using rule-based models configured to determine optimal prediction window lengths based at least in part on breathing measurement data for the prediction window and/or based at least in part on user activity data for the prediction window, using machine learning models configured to determine optimal prediction window lengths, and/or the like. Examples of optimal lengths for periods of times described by prediction windows include one minute, twenty-four hours, ten days, two weeks, and/or the like. In some embodiments, examples of optimal lengths for periods of times described by prediction windows include one breathing cycle, five breathing cycles, ten breathing cycle, one hundred breathing cycles, and/or the like. For example, in some embodiments, in response to determining that n predicted interruption scores in a prediction window satisfies a predicted interruption score threshold, and/or n splinting severity levels in the prediction window satisfies a splinting severity level, the predictive data analysis computing entity 106 performs one or more prediction based actions (e.g., therapeutic intervention). In some embodiments, the techniques discussed herein may be performed using digital incremented or decremented numbers (e.g., via a Bluetooth Low Energy device that is linked to a digital spirometer).

In some embodiments, the therapeutic notifications walks a patient through breathing patterns that build the patients confidence by starting at inspiration levels that build in capacity, ultimately taking the patient through completed lung capacity that has been previously as learned maximum. The challenge may be performed by alternately pushing the patient to higher levels. In some embodiments, the therapeutic notifications indicate on an on-screen waveform indicating the breathing pattern in real time. In some embodiments, the therapeutic notifications identify key pain points (identified by splinting) and notate them in a color such as red. This will allow the patient to visualize the inspirational pattern during the therapy. In some embodiments, the therapeutic notifications identify too slow inspirations or too fast inspirations. In some embodiments, guided sessions will continue at intervals until no splinting or pain is detected.

In accordance with the above-described techniques, various embodiments of the present invention address technical challenges related to efficiently and effectively performing splinting activity detection based at least in part on observed breathing pattern sensory data for a monitored individual. The disclosed techniques improve the efficiency and effectiveness of splinting activity detection by utilizing a splinting activity detection machine learning model that is configured to compare an observed inspiration-expiration waveform pattern that is generated based at least in part on observed breathing pattern sensory data with the one or more expected inspiration-expiration waveform patterns. The splinting activity detection machine learning models utilize comparison operations that may, in at least some embodiments, reduce or eliminate the need for computationally expensive training operations in order to generate the noted splinting activity detection machine learning models. By reducing or eliminating the noted training operations, various embodiments of the present invention: (i) reduces or eliminates the computational operations needed for training and thus improves the computational efficiency of performing splinting activity detection, (ii) reduces or eliminates the need for storage resources to train/generate splinting activity detection machine learning models and thus improves storage efficiency of performing splinting activity detection, and (iii) reduces or eliminates the need for transmitting extensive training data needed to generate splinting activity detection machine learning models and thus improves transmission/network efficiency of performing splinting activity detection. Via the noted advantages, various embodiments of the present invention make substantial technical contributions to the fields of splinting activity detection in particular and healthcare-related predictive data analysis in general.

An exemplary application of various embodiments of the present invention relates to proactively monitoring breathing patterns of atelectasis patients. Atelectasis is one of the most common breathing (respiratory) complications after surgery. Patients generally will experience some form of pain when breathing. Atelectasis causes splinting in the body's effort to avoid pain. Improper breathing exercises or the lack of (with or without an incentive spirometer) can cause complications most commonly resulting in pneumonia, which can lead to death. Besides post-surgical patients, acute lung conditions or even those that are chronic put the patient at risk for lung pain that can result in serious illness or death if the patient does not follow proper lung care guidance. Concerning lung pain due to atelectasis or pleurisy, the patient may not be aware that they are coddling or compensating physically or mentally right away. Older patients and much younger patients at each end of the age spectrum are particularly at risk of this condition.

VI. CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer-implemented method comprising:
identifying, by one or more processors, observed breathing pattern sensory data for a monitored individual;
determining, by the one or more processors, an observed inspiration-expiration waveform pattern based at least in part on the observed breathing pattern sensory data;
generating, by the one or more processors and utilizing a splinting activity detection machine learning model, a predicted interruption score for the observed breathing pattern sensory data, wherein: the predicted interruption score (i) is generated based at least in part on the observed inspiration-expiration waveform pattern and one or more expected inspiration-expiration waveform patterns, and (ii) represents a likelihood that the observed inspiration-expiration waveform pattern represents splinting activity; and
initiating, by the one or more processors, the performance of one or more prediction-based actions based at least in part on the predicted interruption score.

2. The computer-implemented method of claim 1, wherein the observed breathing pattern sensory data comprises a first sensory indicator of a diaphragm expansion for the monitored individual and a second sensory indicator of a diaphragm contraction for the monitored individual.

3. The computer-implemented method of claim 1, wherein:

the one or more expected inspiration-expiration waveform patterns comprise one or more activity severity subsets of the one or more expected inspiration-expiration waveform patterns;

each activity severity subset is associated with an activity severity level of one or more activity severity levels;

the one or more expected inspiration-expiration waveform patterns are selected from the one or more activity severity subsets based at least in part on a target activity severity level for the observed breathing pattern sensory data; and the target activity severity level is determined based at least in part on biometric data associated with the observed breathing pattern sensory data.

4. The computer-implemented method of claim 1, wherein:

each expected inspiration-expiration waveform pattern represents a substantially triangular pattern;

each expected inspiration-expiration waveform pattern comprises a left half-triangular pattern that is associated with a detected inspiration pattern of the observed breathing pattern sensory data; and each expected inspiration-expiration waveform pattern comprises a right half-triangular pattern that is associated with a detected expiration pattern of the observed breathing pattern sensory data.

5. The computer-implemented method of claim 1, wherein comparing the observed inspiration-expiration waveform pattern with a particular expected inspiration-expiration waveform pattern of the one or more expected inspiration-expiration waveform patterns comprises:

determining, by the one or more processors, an observed peak amplitude of the observed inspiration-expiration waveform pattern;

determining, by the one or more processors, an expected peak amplitude of the particular expected inspiration-expiration waveform pattern; and comparing, by the one or more processors, the observed peak amplitude and the expected peak amplitude to determine a difference measure for the observed inspiration-expiration waveform pattern and the particular expected inspiration-expiration waveform pattern.

6. The computer-implemented method of claim 5, wherein the predicted interruption score is determined based at least in part on whether a lowest difference measure associated with the observed inspiration-expiration waveform pattern satisfies a difference measure threshold.

7. The computer-implemented method of claim 1, wherein generating the predicted interruption score includes:

detecting an interruption duration of a detected interruption in an upward progression of the observed inspiration-expiration waveform pattern;

determining a splinting severity level based at least in part on the interruption duration; and determining the predicted interruption score based at least in part on the splinting severity level.

8. The computer-implemented method of claim 1, wherein initiating the performance of the one or more prediction-based actions comprises:

in response to determining that the predicted interruption score satisfies a predicted interruption score threshold, generating user interface data for one or more therapeutic notifications corresponding to the observed inspiration-expiration waveform pattern, wherein the one or more therapeutic notifications are configured to be displayed using a display device of a computing entity associated with the monitored individual.

9. An apparatus comprising one or more processors and at least one memory including program code, the at least one memory and the program code configured to, with the one or more processors, cause the apparatus to at least:

identify observed breathing pattern sensory data for a monitored individual;

determine an observed inspiration-expiration waveform pattern based at least in part on the observed breathing pattern sensory data;

generate, utilizing a splinting activity detection machine learning model, a predicted interruption score for the observed breathing pattern sensory data, wherein: the predicted interruption score (i) is generated based at least in part on the observed inspiration-expiration waveform pattern and one or more expected inspiration-expiration waveform patterns, and (ii) represents a likelihood that the observed inspiration-expiration waveform pattern represents splinting activity; and initiate the performance of one or more prediction-based actions based at least in part on the predicted interruption score.

10. The apparatus of claim 9, wherein the observed breathing pattern sensory data comprises a first sensory indicator of a diaphragm expansion for the monitored individual and a second sensory indicator of a diaphragm contraction for the monitored individual.

11. The apparatus of claim 9, wherein:

the one or more expected inspiration-expiration waveform patterns comprise one or more activity severity subsets of the one or more expected inspiration-expiration waveform patterns;

each activity severity subset is associated with an activity severity level of one or more activity severity levels;

the one or more expected inspiration-expiration waveform patterns are selected from the one or more activity severity subsets based at least in part on a target activity severity level for the observed breathing pattern sensory data; and the target activity severity level is determined based at least in part on biometric data associated with the observed breathing pattern sensory data.

12. The apparatus of claim 9, wherein:

each expected inspiration-expiration waveform pattern represents a substantially triangular pattern;

each expected inspiration-expiration waveform pattern comprises a left half-triangular pattern that is associated with a detected inspiration pattern of the observed breathing pattern sensory data; and each expected inspiration-expiration waveform pattern comprises a right half-triangular pattern that is associated with a detected expiration pattern of the observed breathing pattern sensory data.

13. The apparatus of claim 9, wherein comparing the observed inspiration-expiration waveform pattern with a particular expected inspiration-expiration waveform pattern of the one or more expected inspiration-expiration waveform patterns comprises:

determining an observed peak amplitude of the observed inspiration-expiration waveform pattern;

determining an expected peak amplitude of the particular expected inspiration-expiration waveform pattern; and comparing the observed peak amplitude and the expected peak amplitude to determine a difference measure for the observed inspiration-expiration waveform pattern and the particular expected inspiration-expiration waveform pattern.

14. The apparatus of claim 13, wherein the predicted interruption score is determined based at least in part on whether a lowest difference measure associated with the observed inspiration-expiration waveform pattern satisfies a difference measure threshold.

15. The apparatus of claim 9, wherein generating the predicted interruption score includes:
  detecting an interruption duration of a detected interruption in an upward progression of the observed inspiration-expiration waveform pattern;
  determining a splinting severity level based at least in part on the interruption duration; and
  determining the predicted interruption score based at least in part on the splinting severity level.

16. The apparatus of claim 9, wherein initiating the performance of the one or more prediction-based actions comprises:
  responsive to determining that the predicted interruption score satisfies a predicted interruption score threshold, generating user interface data for one or more therapeutic notifications corresponding to the observed inspiration-expiration waveform pattern, wherein the one or more therapeutic notifications are configured to be displayed using a display device of a computing entity associated with the monitored individual.

17. At least one non-transitory computer-readable storage medium having computer-readable program code portions stored therein, the computer-readable program code portions configured to:
  identify observed breathing pattern sensory data for a monitored individual;
  determine an observed inspiration-expiration waveform pattern based at least in part on the observed breathing pattern sensory data;
  generate, utilizing a splinting activity detection machine learning model, a predicted interruption score for the observed breathing pattern sensory data, wherein: the predicted interruption score (i) is generated based at least in part on the observed inspiration-expiration waveform pattern and one or more expected inspiration-expiration waveform patterns, and (ii) represents a likelihood that the observed inspiration-expiration waveform pattern represents splinting activity; and
  initiate the performance of one or more prediction-based actions based at least in part on the predicted interruption score.

18. The at least one non-transitory computer-readable storage medium of claim 17, wherein the observed breathing pattern sensory data comprises a first sensory indicator of a diaphragm expansion for the monitored individual and a second sensory indicator of a diaphragm contraction for the monitored individual.

19. The at least one non-transitory computer-readable storage medium of claim 17, wherein:
  the one or more expected inspiration-expiration waveform patterns comprise one or more activity severity subsets of the one or more expected inspiration-expiration waveform patterns;
  each activity severity subset is associated with an activity severity level of one or more activity severity levels;
  the one or more expected inspiration-expiration waveform patterns are selected from the one or more activity severity subsets based at least in part on a target activity severity level for the observed breathing pattern sensory data; and
  the target activity severity level is determined based at least in part on biometric data associated with the observed breathing pattern sensory data.

20. The at least one non-transitory computer-readable storage medium of claim 17, wherein:
  each expected inspiration-expiration waveform pattern represents a substantially triangular pattern;
  each expected inspiration-expiration waveform pattern comprises a left half-triangular pattern that is associated with a detected inspiration pattern of the observed breathing pattern sensory data; and
  each expected inspiration-expiration waveform pattern comprises a right half-triangular pattern that is associated with a detected expiration pattern of the observed breathing pattern sensory data.

* * * * *